US012276659B2

(12) United States Patent
Kim et al.

(10) Patent No.: US 12,276,659 B2
(45) Date of Patent: Apr. 15, 2025

(54) COMPOSITIONS AND METHODS FOR PASSIVE OPTICAL BARCODING FOR MULTIPLEXED ASSAYS

(71) Applicant: Slingshot Biosciences, Inc., Emeryville, CA (US)

(72) Inventors: Jeffrey Kim, Berkeley, CA (US); Anh Tuan Nguyen, San Francisco, CA (US); Brandon Miller, Oakland, CA (US)

(73) Assignee: Slingshot Biosciences, Inc., Emeryville, CA (US)

( * ) Notice: Subject to any disclaimer, the term of this patent is extended or adjusted under 35 U.S.C. 154(b) by 150 days.

(21) Appl. No.: 18/105,582

(22) Filed: Feb. 3, 2023

(65) Prior Publication Data

US 2023/0176042 A1 Jun. 8, 2023

Related U.S. Application Data

(62) Division of application No. 17/307,127, filed on May 4, 2021, now Pat. No. 11,598,768.

(Continued)

(51) Int. Cl.
*G01N 33/543* (2006.01)
*C08J 3/075* (2006.01)
(Continued)

(52) U.S. Cl.
CPC .......... *G01N 33/5432* (2013.01); *C08J 3/075* (2013.01); *G01N 15/1434* (2013.01);
(Continued)

(58) Field of Classification Search
CPC ...................... G01N 33/5432; G01N 15/1434
See application file for complete search history.

(56) References Cited

U.S. PATENT DOCUMENTS

| | | | |
|---|---|---|---|
| 3,822,095 | A | 7/1974 | Hirschfeld |
| 3,872,312 | A | 3/1975 | Hirschfeld |

(Continued)

FOREIGN PATENT DOCUMENTS

| | | | |
|---|---|---|---|
| CN | 101245368 A | 8/2008 | |
| CN | 103744185 A | 4/2014 | |

(Continued)

OTHER PUBLICATIONS

Advisory Action issued by The United States Patent and Trademark Office for U.S. Appl. No. 17/155,294, dated Nov. 29, 2021, 5 pages.
(Continued)

*Primary Examiner* — Gailene Gabel
(74) *Attorney, Agent, or Firm* — COOLEY LLP

(57) ABSTRACT

Compositions comprising multiple hydrogel particles having substantially the same diameter, but with each subgrouping of particles from the multiple hydrogel particles having different associated values for one or more passive optical properties that can be deconvoluted using cytometric instrumentation. Each hydrogel particle from the multiple hydrogel particles can be functionalized with a different biochemical or chemical target from a set of targets. A method of preparing hydrogel particles includes forming droplets and polymerizing the droplets, with optional functionalization.

15 Claims, 12 Drawing Sheets

Related U.S. Application Data

(60) Provisional application No. 63/019,478, filed on May 4, 2020.

(51) Int. Cl.
 *G01N 15/1434* (2024.01)
 *G01N 33/53* (2006.01)

(52) U.S. Cl.
 CPC ....... *G01N 33/53* (2013.01); *G01N 33/54313* (2013.01); *C08J 2333/26* (2013.01)

(56) References Cited

U.S. PATENT DOCUMENTS

| | | | |
|---|---|---|---|
| 3,916,205 A | 10/1975 | Kleinerman | |
| 3,937,799 A | 2/1976 | Lewin et al. | |
| 3,947,564 A | 3/1976 | Shannon et al. | |
| 3,975,084 A | 8/1976 | Block | |
| 4,271,123 A | 6/1981 | Curry et al. | |
| 4,295,199 A | 10/1981 | Curry et al. | |
| 4,389,491 A | 6/1983 | Hanamoto et al. | |
| 4,409,335 A | 10/1983 | Hanamoto et al. | |
| 4,448,888 A | 5/1984 | Bleile et al. | |
| 4,511,662 A | 4/1985 | Baran et al. | |
| 4,704,891 A | 11/1987 | Recktenwald et al. | |
| 4,774,189 A | 9/1988 | Schwartz | |
| 4,857,451 A | 8/1989 | Schwartz | |
| 5,093,234 A | 3/1992 | Schwartz | |
| 5,283,079 A | 2/1994 | Wang et al. | |
| 5,395,688 A | 3/1995 | Wang et al. | |
| 5,820,879 A | 10/1998 | Fernandez et al. | |
| 5,841,139 A | 11/1998 | Sostek et al. | |
| 5,888,823 A | 3/1999 | Matsumoto et al. | |
| 6,043,506 A | 3/2000 | Heffelfinger et al. | |
| 6,107,365 A | 8/2000 | Bertozzi et al. | |
| 6,108,082 A | 8/2000 | Pettipiece et al. | |
| 6,214,539 B1 | 4/2001 | Cosand | |
| 6,280,618 B2 | 8/2001 | Watkins et al. | |
| 6,372,813 B1 | 4/2002 | Johnson et al. | |
| 6,516,537 B1 | 2/2003 | Teich et al. | |
| 6,586,176 B1 | 7/2003 | Trnovsky et al. | |
| 6,657,030 B2 | 12/2003 | Vanderbilt | |
| 6,762,055 B2 | 7/2004 | Carver et al. | |
| 6,806,058 B2 | 10/2004 | Jesperson et al. | |
| 6,872,578 B2 | 3/2005 | Watkins et al. | |
| 6,897,072 B1 | 5/2005 | Rich et al. | |
| 7,045,366 B2 | 5/2006 | Huang et al. | |
| RE39,542 E | 4/2007 | Jain et al. | |
| 7,205,156 B2 | 4/2007 | Rich et al. | |
| 7,294,503 B2 | 11/2007 | Quake et al. | |
| 7,314,584 B2 | 1/2008 | Tsutsui et al. | |
| 7,465,538 B2 | 12/2008 | Watkins et al. | |
| 7,479,631 B2 | 1/2009 | Rich et al. | |
| 7,482,161 B2 | 1/2009 | Carver et al. | |
| 7,482,167 B2 | 1/2009 | Sammak et al. | |
| 7,531,357 B2 | 5/2009 | Carver et al. | |
| 7,569,399 B2 | 8/2009 | Watkins et al. | |
| 7,588,942 B2 | 9/2009 | Ho et al. | |
| 7,601,539 B2 | 10/2009 | Kawate | |
| 7,776,927 B2 | 8/2010 | Chu et al. | |
| 7,842,498 B2 | 11/2010 | Um et al. | |
| 8,030,095 B2 | 10/2011 | Harriman | |
| 8,105,845 B2 | 1/2012 | Notcovich et al. | |
| 8,114,580 B2 | 2/2012 | Carver et al. | |
| 8,187,885 B2 | 5/2012 | Purvis, Jr. | |
| 8,415,161 B2 | 4/2013 | Yan et al. | |
| 8,415,173 B2 | 4/2013 | Harriman | |
| 8,451,450 B2 | 5/2013 | Heng | |
| 8,580,530 B2 | 11/2013 | Buffiere et al. | |
| 8,580,531 B2 | 11/2013 | Buffiere et al. | |
| 8,603,828 B2 | 12/2013 | Walker et al. | |
| 8,609,363 B2 | 12/2013 | Heng et al. | |
| 8,704,158 B2 | 4/2014 | Haberstroh et al. | |
| 8,748,183 B2 | 6/2014 | Durack et al. | |
| 9,012,167 B2 | 4/2015 | Dallenne et al. | |
| 9,110,050 B2 | 8/2015 | Likuski et al. | |
| 9,175,421 B2 | 11/2015 | Notcovich et al. | |
| 9,176,154 B2 | 11/2015 | Darmstadt et al. | |
| 9,213,034 B2 | 12/2015 | Walker et al. | |
| 9,217,175 B2 | 12/2015 | Regan et al. | |
| 9,228,898 B2 | 1/2016 | Kiani et al. | |
| 9,417,190 B2 | 8/2016 | Hindson et al. | |
| 9,476,101 B2 | 10/2016 | Pregibon et al. | |
| 9,658,220 B2 | 5/2017 | King et al. | |
| 9,696,257 B2 | 7/2017 | Fox et al. | |
| 9,714,897 B2 | 7/2017 | Kim et al. | |
| 9,804,149 B2 | 10/2017 | Darmstadt et al. | |
| 9,816,931 B2 | 11/2017 | Abate et al. | |
| 9,915,598 B2 | 3/2018 | Kim et al. | |
| 10,067,135 B2 | 9/2018 | Kaul et al. | |
| 10,180,385 B2 | 1/2019 | Fox et al. | |
| 10,191,039 B2 | 1/2019 | King et al. | |
| 10,343,167 B2 | 7/2019 | Esmail et al. | |
| 10,344,100 B1 | 7/2019 | Vashist et al. | |
| 10,392,557 B2 | 8/2019 | Chan | |
| 10,416,070 B1 | 9/2019 | Handique | |
| 10,429,291 B2 | 10/2019 | Fox et al. | |
| 10,481,068 B2 | 11/2019 | Kim et al. | |
| 10,508,990 B2 | 12/2019 | Fox et al. | |
| 10,732,189 B2 | 8/2020 | Buffiere et al. | |
| 10,753,846 B2 | 8/2020 | Kim et al. | |
| 10,942,109 B2 | 3/2021 | Kim et al. | |
| 11,047,845 B1 | 6/2021 | Barry, Jr. et al. | |
| 11,085,036 B2 | 8/2021 | Norberg et al. | |
| 11,118,217 B2 | 9/2021 | Xue et al. | |
| 11,155,809 B2 | 10/2021 | Lebofsky | |
| 11,180,752 B2 | 11/2021 | Wu et al. | |
| 11,186,862 B2 | 11/2021 | Lebofsky et al. | |
| 11,213,490 B2 | 1/2022 | Shoichet et al. | |
| 11,231,355 B2 | 1/2022 | Handique | |
| 11,274,337 B2 | 3/2022 | Xue et al. | |
| 11,300,496 B2 | 4/2022 | Handique | |
| 11,313,782 B2 | 4/2022 | Kim et al. | |
| 11,479,816 B2 | 10/2022 | Lebofsky et al. | |
| 11,506,655 B2 | 11/2022 | Hunsley et al. | |
| 11,598,768 B2 | 3/2023 | Kim | |
| 11,603,556 B2 | 3/2023 | Lebofsky | |
| 11,663,717 B2 | 5/2023 | Barnes et al. | |
| 11,686,661 B2 | 6/2023 | Kim et al. | |
| 11,726,023 B2 | 8/2023 | Kim et al. | |
| 11,747,261 B2 | 9/2023 | Kim et al. | |
| 11,761,877 B2 | 9/2023 | Kim et al. | |
| 11,927,519 B2 | 3/2024 | Kim et al. | |
| 12,038,369 B2 | 7/2024 | Kim et al. | |
| 12,066,369 B2 | 8/2024 | Kim et al. | |
| 2001/0008217 A1 | 7/2001 | Watkins et al. | |
| 2001/0054580 A1 | 12/2001 | Watkins et al. | |
| 2002/0115116 A1 | 8/2002 | Song et al. | |
| 2003/0013116 A1 | 1/2003 | Song et al. | |
| 2003/0022157 A1 | 1/2003 | Zauderer et al. | |
| 2003/0064403 A1 | 4/2003 | Song et al. | |
| 2003/0124371 A1 | 7/2003 | Um et al. | |
| 2003/0132538 A1 | 7/2003 | Chandler | |
| 2003/0190749 A1 | 10/2003 | Surber et al. | |
| 2003/0218130 A1 | 11/2003 | Boschetti et al. | |
| 2003/0224444 A1 | 12/2003 | Sabbadini et al. | |
| 2004/0126904 A1 | 7/2004 | Watkins et al. | |
| 2005/0059086 A1 | 3/2005 | Huang et al. | |
| 2005/0090016 A1 | 4/2005 | Rich et al. | |
| 2005/0112650 A1 | 5/2005 | Chang et al. | |
| 2005/0118230 A1 | 6/2005 | Hill et al. | |
| 2005/0172476 A1 | 8/2005 | Stone et al. | |
| 2005/0176056 A1 | 8/2005 | Sammak et al. | |
| 2005/0208573 A1 | 9/2005 | Bell et al. | |
| 2006/0163385 A1 | 7/2006 | Link et al. | |
| 2006/0223187 A1 | 10/2006 | Carver et al. | |
| 2006/0240560 A1 | 10/2006 | Bakker et al. | |
| 2006/0250616 A1 | 11/2006 | Pettipiece et al. | |
| 2006/0269962 A1 | 11/2006 | Watkins et al. | |
| 2006/0275820 A1 | 12/2006 | Watkins et al. | |
| 2007/0003442 A1 | 1/2007 | Link et al. | |
| 2007/0054119 A1 | 3/2007 | Garstecki et al. | |
| 2007/0082019 A1 | 4/2007 | Huang et al. | |
| 2007/0087348 A1 | 4/2007 | Notcovich et al. | |

(56) References Cited

U.S. PATENT DOCUMENTS

| | | |
|---|---|---|
| 2007/0158547 A1 | 7/2007 | Rich et al. |
| 2007/0178168 A1 | 8/2007 | Ho et al. |
| 2007/0254378 A1 | 11/2007 | Zhang et al. |
| 2007/0259415 A1 | 11/2007 | Zigova et al. |
| 2008/0014589 A1 | 1/2008 | Link et al. |
| 2008/0019921 A1 | 1/2008 | Zhang |
| 2008/0023630 A1 | 1/2008 | Boschetti et al. |
| 2008/0026468 A1 | 1/2008 | Carver et al. |
| 2008/0032405 A1 | 2/2008 | Ho et al. |
| 2008/0044472 A1 | 2/2008 | Garcia et al. |
| 2008/0090737 A1 | 4/2008 | Boschetti |
| 2008/0241262 A1 | 10/2008 | Lee et al. |
| 2009/0148961 A1 | 6/2009 | Luchini et al. |
| 2010/0120059 A1 | 5/2010 | Yan et al. |
| 2010/0178647 A1 | 7/2010 | Carver et al. |
| 2010/0178656 A1 | 7/2010 | Buffiere et al. |
| 2010/0184101 A1 | 7/2010 | Buffiere et al. |
| 2010/0187441 A1 | 7/2010 | Waldbeser et al. |
| 2010/0234252 A1 | 9/2010 | Moradi-Araghi et al. |
| 2010/0285594 A1 | 11/2010 | Purvis, Jr. |
| 2011/0117670 A1 | 5/2011 | Walker et al. |
| 2011/0218123 A1 | 9/2011 | Weitz et al. |
| 2011/0222068 A1 | 9/2011 | Heng |
| 2011/0318820 A1 | 12/2011 | Hinz et al. |
| 2012/0129723 A1 | 5/2012 | Notcovich et al. |
| 2012/0295300 A1 | 11/2012 | Heng et al. |
| 2012/0309651 A1 | 12/2012 | Pregibon et al. |
| 2013/0089883 A1 | 4/2013 | Dallenne et al. |
| 2013/0177973 A1 | 7/2013 | Kondo |
| 2013/0274125 A1 | 10/2013 | Binder et al. |
| 2014/0073532 A1 | 3/2014 | Walker et al. |
| 2014/0100791 A1 | 4/2014 | Darmstadt et al. |
| 2014/0157859 A1 | 6/2014 | Darmstadt et al. |
| 2014/0179808 A1 | 6/2014 | Flanagan |
| 2014/0198313 A1 | 7/2014 | Tracy et al. |
| 2014/0221238 A1 | 8/2014 | Regan et al. |
| 2014/0377334 A1 | 12/2014 | Irvine et al. |
| 2015/0027207 A1 | 1/2015 | Likuski et al. |
| 2015/0094232 A1 | 4/2015 | Abate et al. |
| 2015/0177115 A1* | 6/2015 | Kim .................. G01N 15/14 435/6.1 |
| 2015/0211044 A1 | 7/2015 | Dallenne et al. |
| 2015/0267196 A1 | 9/2015 | Alsberg et al. |
| 2016/0258856 A1 | 9/2016 | Kim et al. |
| 2017/0045436 A1 | 2/2017 | Fox et al. |
| 2017/0159132 A1 | 6/2017 | Okino et al. |
| 2017/0268998 A1 | 9/2017 | Fox et al. |
| 2017/0361322 A1 | 12/2017 | Esmail et al. |
| 2017/0370951 A1 | 12/2017 | Buffiere et al. |
| 2018/0172687 A1 | 6/2018 | Kaul et al. |
| 2018/0216171 A1 | 8/2018 | Xue et al. |
| 2018/0275040 A1* | 9/2018 | Kim .................. G01N 15/1012 |
| 2018/0371525 A1 | 12/2018 | Lebofsky et al. |
| 2019/0145881 A1 | 5/2019 | Fox et al. |
| 2019/0154707 A1 | 5/2019 | Flamini et al. |
| 2019/0249171 A1 | 8/2019 | Wu et al. |
| 2019/0293546 A1 | 9/2019 | Handique |
| 2020/0056231 A1 | 2/2020 | Lebofsky et al. |
| 2020/0115675 A1 | 4/2020 | Pathak et al. |
| 2020/0150020 A1 | 5/2020 | Kim et al. |
| 2020/0206145 A1 | 7/2020 | Shi et al. |
| 2020/0209064 A1 | 7/2020 | Owsley et al. |
| 2020/0232979 A1 | 7/2020 | Revzin et al. |
| 2020/0249242 A1 | 8/2020 | Batxelli-Molina et al. |
| 2020/0332354 A1 | 10/2020 | Xue et al. |
| 2020/0363434 A1 | 11/2020 | Buffiere et al. |
| 2020/0399428 A1 | 12/2020 | Kleine-Brüggeney et al. |
| 2020/0400546 A1 | 12/2020 | Kim et al. |
| 2020/0408747 A1 | 12/2020 | Zur Megede et al. |
| 2021/0040567 A1 | 2/2021 | Handique et al. |
| 2021/0130880 A1 | 5/2021 | Lebofsky |
| 2021/0190740 A1 | 6/2021 | Scolari et al. |
| 2021/0231552 A1 | 7/2021 | Kim et al. |
| 2021/0247294 A1 | 8/2021 | Handique |
| 2021/0341469 A1 | 11/2021 | Kim et al. |
| 2022/0042077 A1 | 2/2022 | Lebofsky et al. |
| 2022/0065878 A1 | 3/2022 | Lee |
| 2022/0154266 A1 | 5/2022 | Xue et al. |
| 2022/0178810 A1 | 6/2022 | Kim et al. |
| 2022/0213530 A1 | 7/2022 | Larson et al. |
| 2022/0260476 A1 | 8/2022 | Kim et al. |
| 2022/0364976 A1 | 11/2022 | Kim et al. |
| 2023/0012786 A1 | 1/2023 | Lebofsky et al. |
| 2023/0062518 A1 | 3/2023 | Ebrahim et al. |
| 2023/0067460 A1 | 3/2023 | Nguyen et al. |
| 2023/0152202 A1 | 5/2023 | Kim et al. |
| 2023/0266223 A1 | 8/2023 | Kim et al. |
| 2024/0053248 A1 | 2/2024 | Kim et al. |
| 2024/0060038 A1 | 2/2024 | Nguyen et al. |
| 2024/0219382 A1 | 7/2024 | Ahn et al. |
| 2024/0269185 A1 | 8/2024 | Nguyen et al. |
| 2024/0319067 A1 | 9/2024 | Kim et al. |

FOREIGN PATENT DOCUMENTS

| | | |
|---|---|---|
| CN | 104641217 A | 5/2015 |
| EP | 3585364 A1 | 1/2020 |
| JP | H07196916 A | 8/1995 |
| JP | 2002510541 A | 4/2002 |
| JP | 2005281470 A | 10/2005 |
| JP | 2007114026 A | 5/2007 |
| JP | 2010265291 A | 11/2010 |
| JP | 2012011269 A | 1/2012 |
| JP | 2013520530 A | 6/2013 |
| JP | 2013155358 A | 8/2013 |
| JP | 2014058557 A | 4/2014 |
| JP | 2014508516 A | 4/2014 |
| JP | 2015530361 A | 10/2015 |
| WO | WO-8910566 A1 | 11/1989 |
| WO | WO-0008212 A1 | 2/2000 |
| WO | WO-0132829 A2 | 5/2001 |
| WO | WO-03000014 A2 | 1/2003 |
| WO | WO-2005013896 A2 | 2/2005 |
| WO | WO-2006003423 A2 | 1/2006 |
| WO | WO-2006078841 A1 | 7/2006 |
| WO | WO-2006096571 A2 | 9/2006 |
| WO | WO-2008115653 A2 | 9/2008 |
| WO | WO-2008121342 A2 | 10/2008 |
| WO | WO-2010025190 A1 | 3/2010 |
| WO | WO-2010025988 A1 | 3/2010 |
| WO | WO-2011098407 A1 | 8/2011 |
| WO | WO-2012033811 A1 | 3/2012 |
| WO | WO-2013113670 A1 | 8/2013 |
| WO | WO-2018108341 A1 | 6/2018 |
| WO | WO-2020037214 A1 | 2/2020 |
| WO | WO-2021154900 A1 | 8/2021 |
| WO | WO-2023215886 A1 | 11/2023 |

OTHER PUBLICATIONS

Bele, Marjan, Olavi Siiman and Egon Matjevic, "Preparation and flow cytomelry of uniform silica-fluorescent dye microspheres." Journal of colloid and interface science 254(2):274-282 (2002).

Extended European Search Report issued by the European Patent Office for Application No. 16749674.4, dated Sep. 6, 2018, 12 pages.

Final Office Action issued by The United States Patent and Trademark Office for U.S. Appl. No. 17/155,294, dated Jul. 1, 2021, 15 pages.

Final Office Action issued by The United States Patent and Trademark Office for U.S. Appl. No. 13/858,912, dated Jan. 11, 2017, 15 pages.

Final Office Action issued by The United States Patent and Trademark Office for U.S. Appl. No. 15/625,394, dated Jun. 12, 2019, 10 pages.

First Examination Report Issued by the Indian Patent Office for Application No. 201737028044, dated Feb. 26, 2021, 6 pages.

Fourth Office Action issued by the Chinese Patent Office for Application No. 201680019908.4, dated Sep. 18, 2021, 4 pages including English translation.

(56) References Cited

OTHER PUBLICATIONS

Hasegawa, Urara et al. "Nanogel-quanlum dot hybrid nanoparticles for live cell imaging." Biochemical and biophysical esearch communications 331(4):917-921 (2005).
Higuchi, A., et al., "Design of polymeric materials for culturing human pluripotent stem cells: Progress toward feeder-free and xeno-free culturing," Progress in Polymer Science, Jul. 2014, vol. 39 (7), pp. 1348-1374, XP028865323.
International Search Report and Written Opinion for International Patent Application No. PCT/US21/014538, dated Apr. 8, 2021, 19 pages.
International Search Report and Written Opinion for International Patent Application No. PCT/US21/030590, dated Jul. 26, 2021, 13 pages.
International Search Report and Written Opinion for International Application No. PCT/US2022/048283 dated Feb. 14, 2023, 14 pages.
International Search Report and Written Opinion for International Patent Application No. PCT/US2016/017029, mailed May 19, 2016, 8 pages.
Kim, Jin-Woong et al., "Fabrication of Monodisperse Gel Shells and Functional Microgels in Microfluidic Devices," Angew. Chem. Int. Ed. 46:819-1822 (2007).
Lee, Ki-Chang and Lee, Sang-Yun, "Preparation of Highly Cross-Linked, Monodisperse Poly (methyl methacrylate) Microspheres by Dispersion Polymerization; Part II. Semi-continuation Processes," Macromolecular Research 6(4):293-302 (2008).
Liu, A.L., et al., "Methods for Generating Hydrogel Particles for Protein Delivery," Annals of Biomedical Engineering, Jun. 2016, vol. 44 (6), pp. 1946-1958, XP035897969.
Luchini, Alessandra et al. "Smart hydrogel particles: biomarker harvesting: one-step affinity purification, size exclusion, and protection against degradation." Nano letters 8(1): 350-361 (2008).
Non-Final Office Action issued by The United States Patent and Trademark Office for U.S. Appl. No. 13/858,912, dated Jun. 6, 2016, 27 pages.
Non-Final Office Action issued by The United States Patent and Trademark Office for U.S. Appl. No. 17/155,294, dated Mar. 22, 2021, 8 pages.
Non-Final Office Action issued by The United States Patent and Trademark Office for U.S. Appl. No. 15/018,769, dated Mar. 9, 2017, 11 pages.
Non-Final Office Action issued by The United States Patent and Trademark Office for U.S. Appl. No. 15/145,856, dated Apr. 6, 2017, 13 pages.
Non-Final Office Action issued by The United States Patent and Trademark Office for U.S. Appl. No. 15/625,394, dated Dec. 13, 2019, 9 pages.
Non-Final Office Action issued by The United States Patent and Trademark Office for U.S. Appl. No. 15/625,394, dated Feb. 8, 2019, 16 pages.
Non-Final Office Action issued by The United States Patent and Trademark Office for U.S. Appl. No. 15/895,307, dated Jul. 18, 2018, 13 pages.
Non-Final Office Action issued by The United States Patent and Trademark Office for U.S. Appl. No. 16/684,694, dated Sep. 29, 2020, 17 pages.
Office Action issued by the Japanese Patent Office for Application No. 2020-72811, May 25, 2021, 7 pages including English translation.
Office Action issued by the Canadian Patent Office for Application No. 2,975,301, dated Feb. 10, 2022, 3 pages.
Office Action issued by the Chinese Patent Office for Application No. 201680019908.4, dated Mar. 25, 2021, 24 pages including English translation.
Office Action issued by the European Patent Office for Application No. 16749674.4, dated Apr. 20, 2021, 10 pages.
Office Action issued by the Japanese Patent Office for Application No. 2017-559788, dated Oct. 17, 2019, 12 pages including English translation.
Office Action issued by the Korean Patent Office for Application No. 10-2022-7028984, dated Oct. 6, 2022, 6 pages including English translation.
Office Action issued by the Taiwanese Patent Office for Application No. 105104380, dated Dec. 6, 2019, 9 pages (including English translation).
Patanarut, Alexis et al., "Synthesis and characterization of hydrogel particles containing Cibacron Blue F3G-A." Colloids and Surfaces A: Physicochemical and Engineering Aspects 362(1):8-19 (2010).
Pérez-Luna, V.H., et al., "Encapsulation of Biological Agents in Hydrogels for Therapeutic Applications," Gels, Jul. 11, 2018, vol. 4 (3), pp. 61, XP093020197.
Proll, Guenther et al. "Potential of label-free detection in high-content-screening applications." Journal of Chromatography A 1116(1):2-8 (2007).
Second Office Action issued by the Chinese Patent Office for Application No. 201680019908.4, dated Mar. 30, 2020, 27 pages including English translation.
Taiwanese Office Action for Application No. TW20130008837 dated Nov. 4, 2021, 6 pages.
Third Office Action issued by the Chinese Patent Office for Application No. 201680019908.4, dated Oct. 12, 2020, 23 pages including English translation.
Tomczak, Nikodem et al., "Designer polymer-quantum dot architectures." Progress in Polymer Science 34:393-430 (2009).
Ugelstad, J.and Mork, P.C., "Swelling of Oligomer-Polymer Particles. New Methods of Preparation of Emulsions and Polymer Dispersions," Advances in Colloid and Interface Sciences, 13:101-140 (1980).
Atkin-Smith et al., "Isolation of cell type-specific apoptotic bodies by fluorescence-activated cell sorting," Scientific Reports, vol. 7, No. 1, Feb. 1, 2017, pp. 1-7.
Chen, M., et al., "Initiator caspases in apoptosis signaling pathways", Apoptosis (London), Aug. 1, 2002, pp. 313-319, DOI: 10.1023/A:1016167228059.
Jain et al. Zwitterionic Hydrogels Based on a Degradable Disulfide Carboxybetaine Cross-Linker, Langmuir 2019, 35, 1864-1871 (Year: 2019).
Jin et al., "Overview of cell death 1-124 signaling pathways", Cancer Biology &G Therapy, vol. 4, No. 2, Feb. 2, 2005, pp. 147-171, DOI: 10.4161/cbt.4.2.1508.
Liu, Z. et al., Recent Advances on Magnetic Sensitive Hydrogels in Tissue Engineering, Frontiers in Chemistry, vol. 8 , Article 124, pp. 1-17, (Mar. 2020).
Shastri, V.P., et al., "Non-Degradable Biocompatible Polymers in Medicine: Past, Present and Future", Current Pharmaceutical Biotechnology, Bentham Science Publishers, NL, vol. 4, No. 5, Jan. 1, 2003, pp. 331-337.
Wallberg et al., "Analysis of Apoptosis and Necroptosis by Fluorescence-Activated Cell Sorting," Cold Spring Harbor Protocol, vol. 2016, No. 4, Apr. 1, 2016, 7 pages.

\* cited by examiner

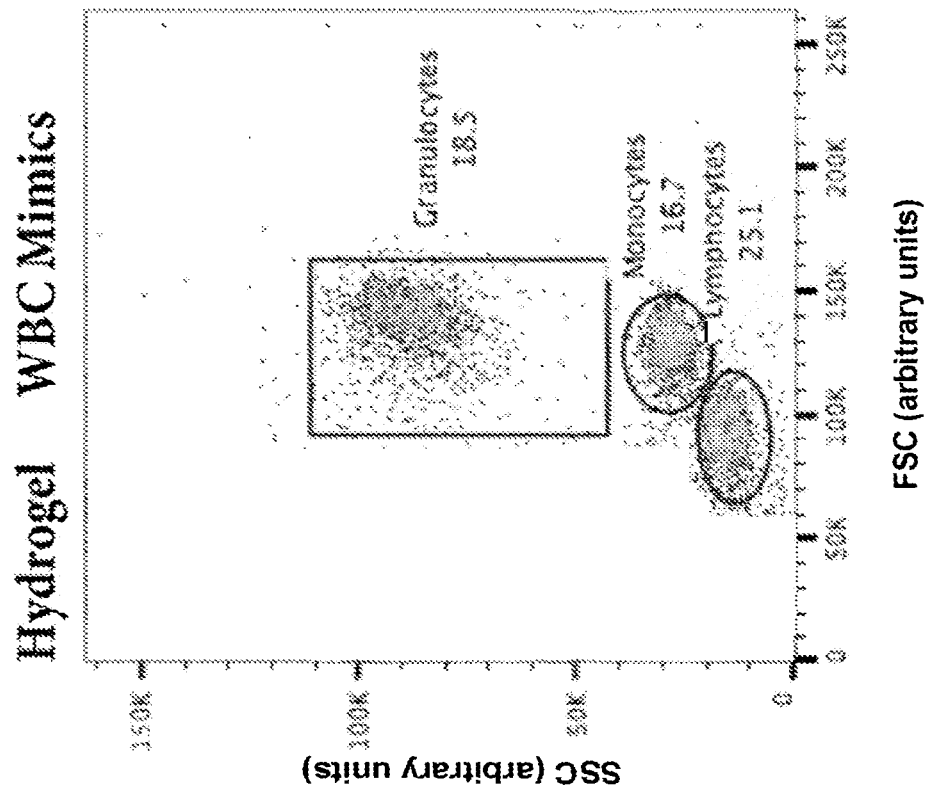
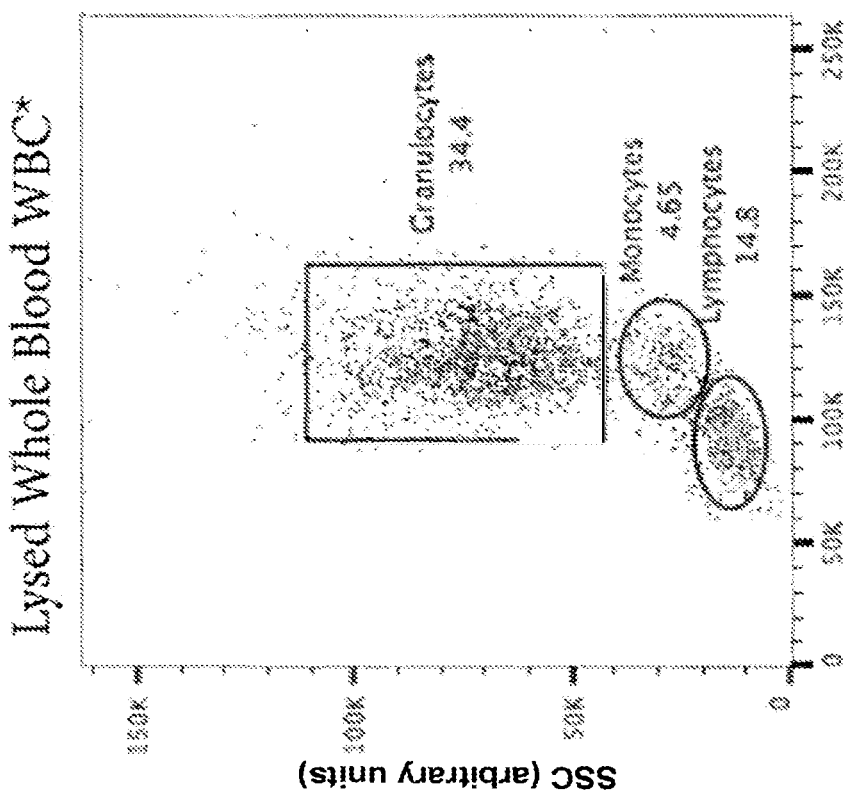
FIG. 8B
FIG. 8A

COMPOSITIONS AND METHODS FOR PASSIVE OPTICAL BARCODING FOR MULTIPLEXED ASSAYS

CROSS REFERENCE TO RELATED APPLICATIONS

This application is a Divisional of U.S. patent application Ser. No. 17/307,127, filed May 4, 2021 and titled "Compositions and Methods for Passive Optical Barcoding for Multiplexed Assays," which claims priority to and the benefit of U.S. Provisional Patent Application No. 63/019,478, filed May 4, 2020 and titled "Compositions and Methods for Passive Optical Barcoding for Multiplexed Assays," the disclosures of each of which are incorporated by reference herein in their entireties.

FIELD

The present disclosure relates to optically barcoding beads by engineering the passive optical properties of a hydrogel polymer, and uses thereof.

BACKGROUND

Flow cytometry and high-throughput cytometric analysis (e.g., high-content imaging) are techniques that allow for the rapid separation, counting, and characterization of individual cells, and are routinely used in clinical and laboratory settings for a variety of applications. Cytometric devices are known in the art and include commercially available devices for performing flow cytometry and FACS, hematology, and high-content imaging.

SUMMARY

In some embodiments, a composition comprises a hydrogel particle having passive optical properties (e.g., FSC and/or SSC) that are deliberately engineered, or "modulated," without altering the size (e.g., the diameter) of the particle itself. The engineered hydrogels can then be used for multiplexing, using passive optical properties, optionally in combination with one or more additional properties, such as fluorescence, in order to perform a multiplexed assay (e.g., chemical or biochemical) in a single reaction that can be deconvoluted based on the passive optical properties of the individual bead populations.

In some embodiments, a method for producing a hydrogel particle includes forming droplets and polymerizing the droplets, with optional functionalization. The method results in hydrogel particles having substantially the same diameter, but different associated pre-determined optical properties (e.g., passive optical properties) that can be deconvoluted using cytometric instrumentation.

In some embodiments, a method is provided for multiplexing assays. The method includes using a population of multiple hydrogel particles with unique passive optical properties in a single assay. Each hydrogel particle from the multiple hydrogel particles having a unique associated one or more biochemical targets. The population of multiple hydrogel particles is assayed and the hydrogel particles and/or the biochemical targets are segregated based on their passive optical properties. The results of a multiplexed assay are then determined, based on the passive optical properties. Methods set forth herein allow for high-dimensional (>1) multiplexed assays to be performed in a single reaction, for example using high throughput cytometric measurements.

BRIEF DESCRIPTION OF THE DRAWINGS

It is to be understood that the drawings primarily are for illustrative purposes and are not intended to limit the scope of the subject matter described herein.

FIGS. 7A-7B demonstrate the ability to perform biochemical multiplexing and demultiplexing using passive optical properties as a primary deconvolution variable, according to some embodiments.

FIG. 8A is a plot of white blood cell counts for an example population of lysed whole blood, and FIG. 8B is a plot of counts for hydrogel particles with tuned passive optical properties, according to an experimental example as an elegant demonstration of optical tuning for a biologically-relevant target population.

FIGS. 9A-9B show that side scatter can be tuned independently of forward scatter, according to an experimental example.

FIGS. 10A-10C show that forward scatter increases with negligible impact on side scatter, with increasing percentages of acrylamide:bis-acrylamide, according to an experimental example.

DETAILED DESCRIPTION

Figure 1:
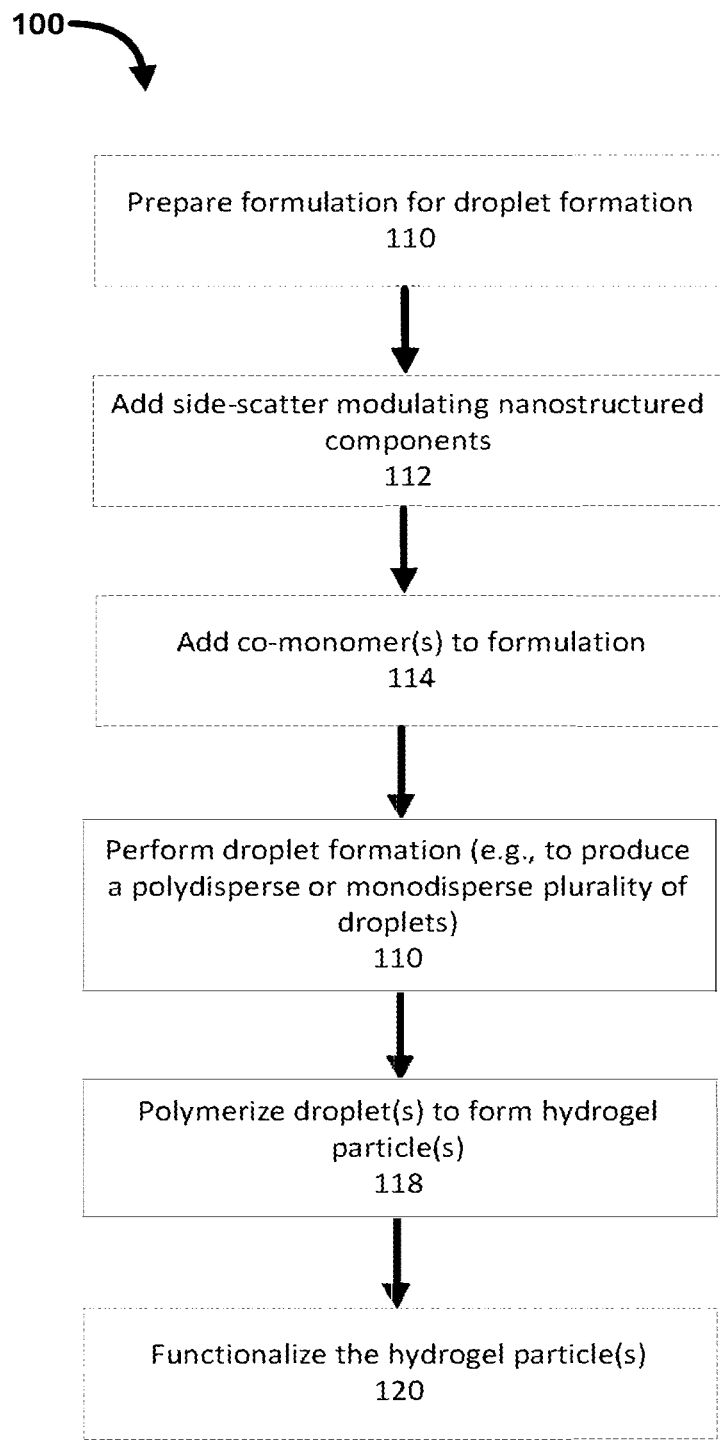
FIG. 1 is a flow diagram showing a method for preparing hydrogel particles, according to some embodiments.

Flow cytometry and high-throughput cytometric analysis can also be used to assay beads (e.g., for biochemical measurements). In some such implementations, a beam of light is directed onto a focused stream of liquid containing the beads. Multiple detectors are then aimed at the point where the stream passes through the light beam, with one detector in line with the light beam (e.g., to detect forward scatter ("FSC")) and several detectors perpendicular to the light beam (e.g., to detect side scatter ("SSC")). FSC and SSC measurements are typically referred to as "passive optical properties." For particles such as cells (e.g., human cells), FSC typically correlates with cell volume, while SSC typically correlates with the inner complexity, or granularity, of the particle (e.g., shape of the nucleus, the amount and type of cytoplasmic granules, or the membrane roughness). As a result of these correlations, different specific cell types can exhibit different FSC and SSC, such that cell types can be distinguished from one another based on their passive optical properties in flow cytometry. These measurements—FSC and SSC—form the basis of cytometric analysis in clinical and research settings. Most synthetic or polymer products used in such cellular analyses are made of (or substantially comprise) polystyrene or latex—opaque polymers that generally have fixed FSC and SSC values based on the diameter of the particle itself. As such, polystyrene particles of the same diameter generally cannot be distinguished from one another based on passive optical properties (FSC and SSC) alone.

To distinguish subpopulations of similarly-sized polystyrene particles from one another, a fluorophore can be added to the particle, allowing for multiplexed (e.g., multi-color) assays. By combining different fluorophores at different concentrations into a single bead, one can create a unique identifier that allows the bead to be distinguished from within a population of distinctly stained beads. When combined with unique assay targets, fluorescently barcoded bead populations such can facilitate the simultaneous assaying of multiple targets (referred to herein as "biochemical multiplexing"). Known products, such as Luminex beads, however, are limited to fluorescent multiplexing because they are made of polystyrene, which as noted above, has fixed passive optical properties. In addition to the material limitations of existing products made of polystyrene, the instruments used to measure such beads typically have a fixed and limited number of fluorescence detectors, placing a limit on the number of dimensions/targets a fluorescence-driven multiplexing strategy can address. Modern biochemical assays stand to benefit from additional dimensions of multiplexing, but are limited by instrument detector availability. As such, there is a need for a product that allows for additional and orthogonal dimensions of multiplexing using passive optical properties. Embodiments set forth herein address this need through passive optical barcoding of hydrogel substrates.

Some known products, such as LEGENDplex (BioLegend), use particles of different sizes to perform>1 plex assays. Although the populations of beads in such products may be distinguishable via their passive optical properties (LEGENDplex, BioLegend), they inherently possess different surface areas, hydrodynamic, and biochemical properties (e.g. concentrations of analytes) as a result of the size differences, leading to suboptimal assay performance and non-quantitative measurements.

General Overview

In view of the fluidic conditions that exist within flow cytometers and high-content imaging systems, particles used for biochemical assays or calibration typically fall within a limited size range to avoid particle settling and related clogging of the fluidics (which can occur with larger particles), and/or to avoid particles floating to the surface of a liquid suspension (which can occur with small particles, making effective sampling challenging). This size restriction limits the forward scattering range that polystyrene particles can elicit. Unlike polystyrene particles, hydrogel particles disclosed herein can exhibit a variety of different optical scatter properties while remaining a fixed diameter, thereby facilitating the optimization of fluidic properties and the introduction of additional dimensions of multiplexing.

FIG. 1 is a flow diagram showing a method for preparing hydrogel particles, according to some embodiments. As shown in FIG. 1, the method 100 includes droplet formation at 110 (e.g., to produce a polydisperse plurality of droplets or a monodisperse plurality of droplets, as described herein). At 112, one or more surfactants are optionally added to the droplets, and at 114, one or more co-monomers are added to the droplets. The droplets are then polymerized, at 116, to form the hydrogel particles, which are optionally subsequently functionalized, at 118 (e.g., with one or more chemical side groups or fluorescent dyes, as discussed further below).

Figure 2:
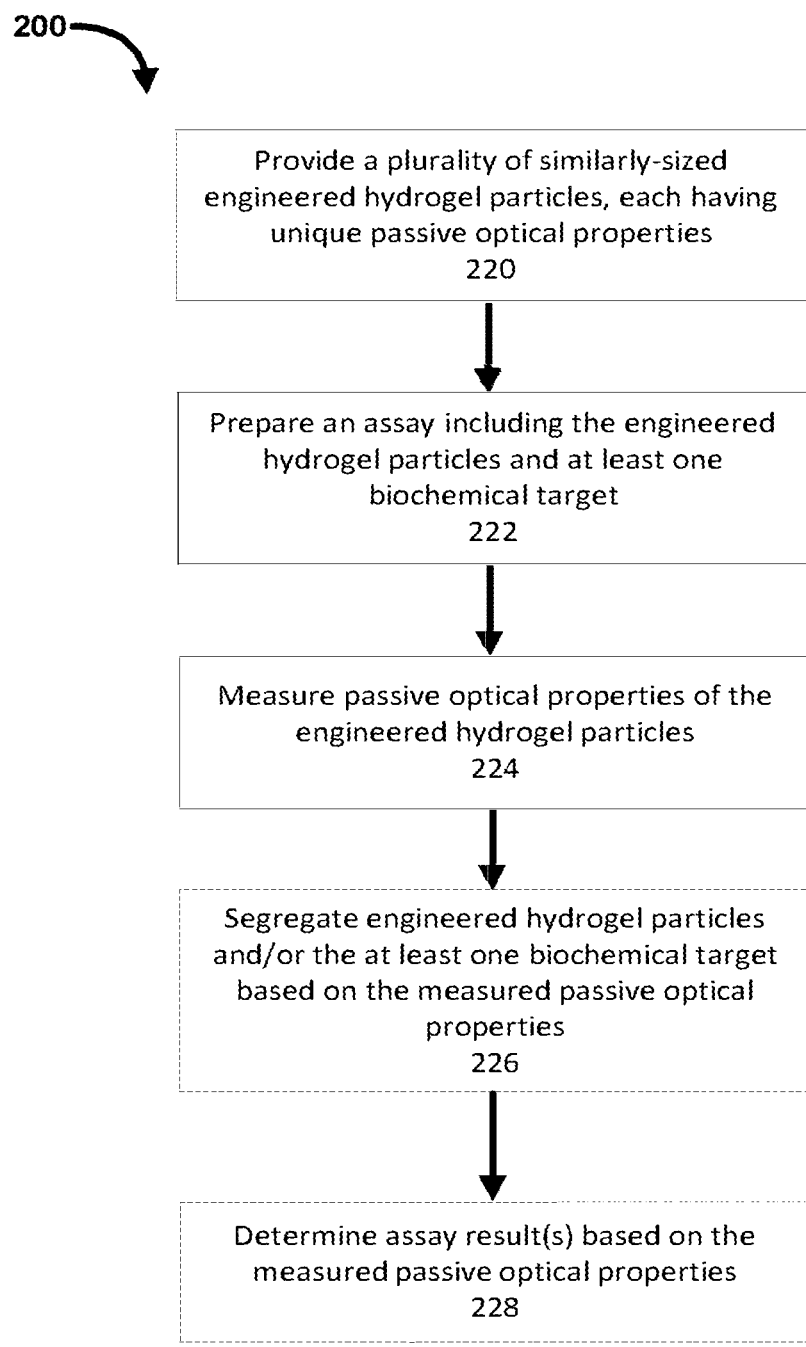
FIG. 2 is a flow diagram showing a method for performing biochemical multiplexing, according to some embodiments.

FIG. 2 is a flow diagram showing a method for performing biochemical multiplexing, according to some embodiments. As shown in FIG. 2, the method 200 includes providing a plurality of engineered hydrogel particles, at 220, each engineered hydrogel particle from the plurality of engineered hydrogel particles having its own unique passive optical properties. The engineered hydrogel particles can be transparent or semi-transparent. At 222, an assay is prepared, including the engineered hydrogel particles and at least one biochemical target. At 224, one or more passive optical properties of the engineered hydrogel particles are measured. Based on these measurements, the engineered hydrogel particles and/or the at least one biochemical target can be segregated, at 226, and/or assay results can be determined, at 228.

Figure 3A:
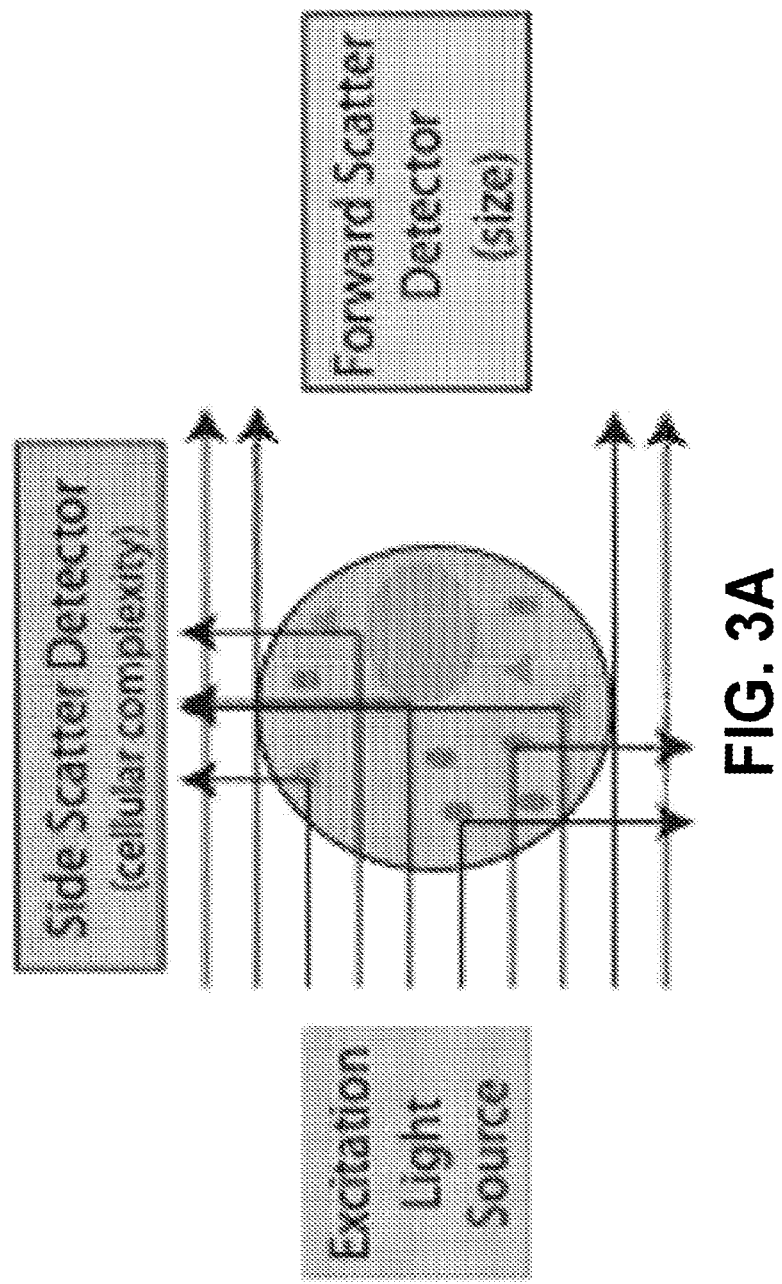
FIG. 3A is a diagram illustrating the optical properties of a cell and the disclosed hydrogel particles (A), according to some embodiments.
Figure 3B:
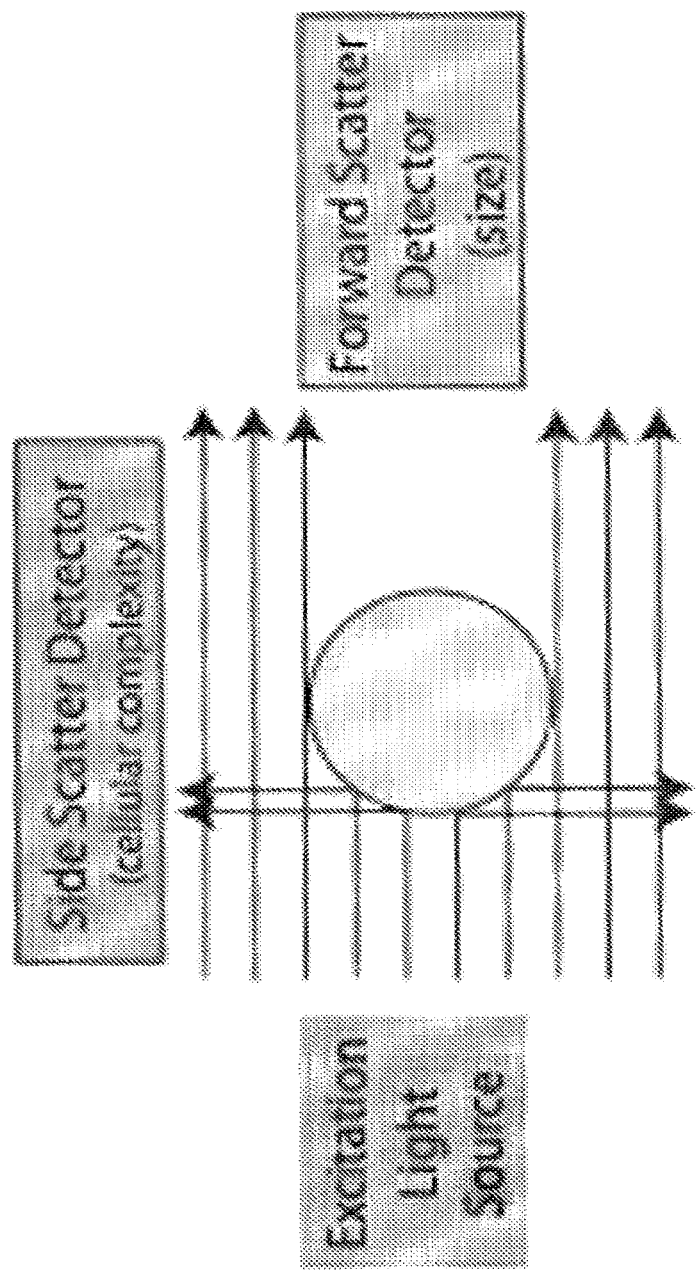
FIG. 3B is a diagram illustrating the optical properties of polystyrene beads (B,C).

FIG. 3A is a diagram illustrating the optical properties of a cell and the disclosed hydrogel particles, according to some embodiments. As shown in FIG. 3A, the engineered hydrogels described herein are semi-transparent, allowing internal features thereof (i.e., cellular complexity) to be resolved using a side scatter (SSC) detector. By contrast, FIG. 3B is a diagram illustrating the optical properties of polystyrene beads. In contrast with FIG. 3A, the polystyrene beads of FIG. 3B are opaque and have a fixed SSC that is determined by their diameter and that is not impacted by (i.e., does not change based on) internal features thereof. As such, polystyrene particles are of limited utility in the two most important passive optical measurements used in flow cytometry: FSC and SSC, which measure the size and complexity of the target, respectively. Due to these limitations of polystyrene, users must typically rely on fluorescence alone for multiplexed immunophenotyping experiments.

In some embodiments set forth herein, a composition comprises a hydrogel particle that is engineered to have passive optical properties that can be distinguished from the optical properties of other particles (e.g., hydrogel particles) of the same diameter, using FSC and SSC alone. The inventors have unexpectedly discovered that optical properties of a hydrogel particle can be independently modulated by altering the composition of the hydrogel particle. For example, SSC can be modulated without substantially affecting FSC, and vice versa (i.e., FSC can be modulated without substantially affecting SSC). Furthermore, the optical properties (e.g., refractive index) of hydrogel particles can be tuned without having a substantial effect on density or on the size of the particles themselves. This is a surprising and useful feature, as these properties allow for multiple particles of the same size to be "encoded" with specific FSC/SSC ratios, and later deconvoluted using detectors such as the detectors found on all cytometric instrumentation, including low-cost instrumentation without fluorescent measurement capabilities.

In some embodiments, a method of producing a hydrogel particle results in the hydrogel particle having pre-determined optical properties. In some embodiments, a method of multiplexing assays includes using a plurality (or "population") of hydrogel particles with unique passive optical properties, each having unique biochemical targets, in a single assay. One or more passive optical properties of the population are measured, and the population and/or the biochemical targets are segregated based on the measured passive optical properties. The results of the multiplexed assay can be generated based on the measured passive optical properties. The foregoing procedure and the engineered nature of the hydrogel particles facilitate performing high-dimensional multiplexed assays in a single reaction, and the segregation of the hydrogel particles and/or the biochemical targets using high throughput cytometric measurements.

Hydrogels

Hydrogel particles set forth herein comprise a hydrogel. A hydrogel is a material comprising a macromolecular three-dimensional network that allows it to swell when in the presence of water, and to shrink in the absence of (or by reduction of the amount of) water, but not to dissolve in water. The swelling, i.e., the absorption of water, is a consequence of the presence of hydrophilic functional groups attached to or dispersed within the macromolecular network. Cross-links between adjacent macromolecules result in the aqueous insolubility of these hydrogels. The cross-links may be due to chemical bonding (i.e., covalent bonds) or physical bonding (i.e., Van Der Waal forces, hydrogen-bonding, ionic forces, etc.). While some in the polymer industry may regard the macromolecular material(s) set forth hereinto be a "xerogel" in the dry state and a "hydrogel" in the hydrated state, for purposes of the present disclosure, the term "hydrogel" will refer to the macromolecular material whether dehydrated or hydrated. A characteristic of a hydrogel that is of particular value is that the material retains its general shape/morphology, whether dehydrated or hydrated. Thus, if the hydrogel has an approximately spherical shape in the dehydrated condition, it will be spherical in the hydrated condition.

Hydrogels set forth herein can comprise greater than about 30%, greater than about 40%, greater than about 50%, greater than about 55%, greater than about 60%, greater than about 65%, greater than about 70%, greater than about 75%, greater than about 80%, or greater than about 85% water.

In some embodiments, synthetic hydrogels can be prepared by polymerizing a monomeric material ("hydrogel monomer") to form a backbone, and cross-linking the backbone with a cross-linking agent. Suitable hydrogel monomers include (but are not limited to) the following: lactic acid, glycolic acid, acrylic acid, 1-hydroxyethyl methacrylate, ethyl methacrylate, propylene glycol methacrylate, acrylamide, N-vinylpyrrolidone, methyl methacrylate, glycidyl methacrylate, glycol methacrylate, ethylene glycol, fumaric acid, and the like. Suitable cross-linking agents include (but are not limited to)tetraethylene glycol dimethacrylate and N,N'-15 methylenebisacrylamide. In some embodiments, a hydrogel particle is produced via the polymerization of acrylamide.

In some embodiments, a hydrogel comprises a mixture of at least one monofunctional monomer and at least one bifunctional monomer.

A monofunctional monomer can be a monofunctional acrylic monomer. Non-limiting examples of monofunctional acrylic monomers are acrylamide; methacrylamide; N-alkylacrylamides such as N-ethylacrylamide, N-isopropylacrylamide or N-tert-butylacrylamide; N-alkylmethacrylamides such as N-ethylmethacrylamide or N-isopropylmethacrylamide; N,N-dialkylacrylamides such as N,N-dimethylacrylamide and N,N-diethyl-acrylamide; N-[(dialkylamino)alkyl]acrylamides such as N-[3 dimethylamino)propyl] acrylamide or N-[3-(diethylamino)propyl]acrylamide; N-[(dialkylamino)alkyl]methacrylamides such as N-[3-dimethylamino)propyl]methacrylamide or N-[3-(diethylamino) propyl]methacrylamide; (dialkylamino)alkyl acrylates such as 2-(dimethylamino)ethyl acrylate, 2-(dimethylamino)propyl acrylate, or 2-(diethylamino)ethyl acrylates; and (dialkylamino)alkyl methacrylates such as 2-(dimethylamino) ethyl methacrylate.

A bifunctional monomer is any monomer that can polymerize with a monofunctional monomer of the disclosure to form a hydrogel as described herein that further contains a second functional group that can participate in a second reaction, e.g., conjugation of a fluorophore.

In some embodiments, a bifunctional monomer is selected from the group consisting of: allyl alcohol, allyl isothiocyanate, allyl chloride, and allyl maleimide.

A bifunctional monomer can be a bifunctional acrylic monomer. Non-limiting examples of bifunctional acrylic monomers are N,N'-methylenebisacrylamide, N,N'-methylenebismethacrylamide, N,N'-ethylenebiscrylamide, N,N'-ethylenebis-methacrylamide, N,N'propylenebisacrylamide and N,N'-(1,2-dihydroxyethylene)bisacrylamide.

Higher-order branched chain and linear co-monomers can be substituted in the polymer mix to adjust the refractive index while maintaining polymer density, as described in U.S. Pat. No. 6,657,030, titled "High Refractive Index Hydrogel Compositions for Ophthalmic Implants," the content of which is incorporated herein by reference in its entirety, for all purposes.

In some embodiments, a hydrogel comprises a molecule that modulates the optical properties of the hydrogel. Molecules capable of altering optical properties of a hydrogel are discussed further below.

Naturally-occurring hydrogels useful for embodiments set forth herein include various polysaccharides available or derived from natural sources, such as plants, algae, fungi, yeasts, marine invertebrates and arthropods. Non-limiting examples of polysaccharides suitable for use in the embodiments set forth herein include (but are not limited to) agarose, dextrans, chitin, cellulose-based compounds, starch, derivatized starch, and the like. Such polysaccharides may include pluralities of repeating glucose units as a major portion of the polysaccharide backbone.

Polymerization of a hydrogel can be initiated by a persulfate. The persulfate can be any water-soluble persulfate. Non-limiting examples of water soluble persulfates are ammonium persulfate and alkali metal persulfates. Alkali metals include lithium, sodium and potassium. In some preferred embodiments, the persulfate is ammonium persulfate or potassium persulfate.

Polymerization of a hydrogel can be accelerated by an accelerant. The accelerant can be a tertiary amine. The tertiary amine can be any water-soluble tertiary amine. Preferably, the tertiary amine is N,N,N',N'tetramethylethylenediamine (TEMED) or 3-dimethylamino)propionitrile.

Figure 4:
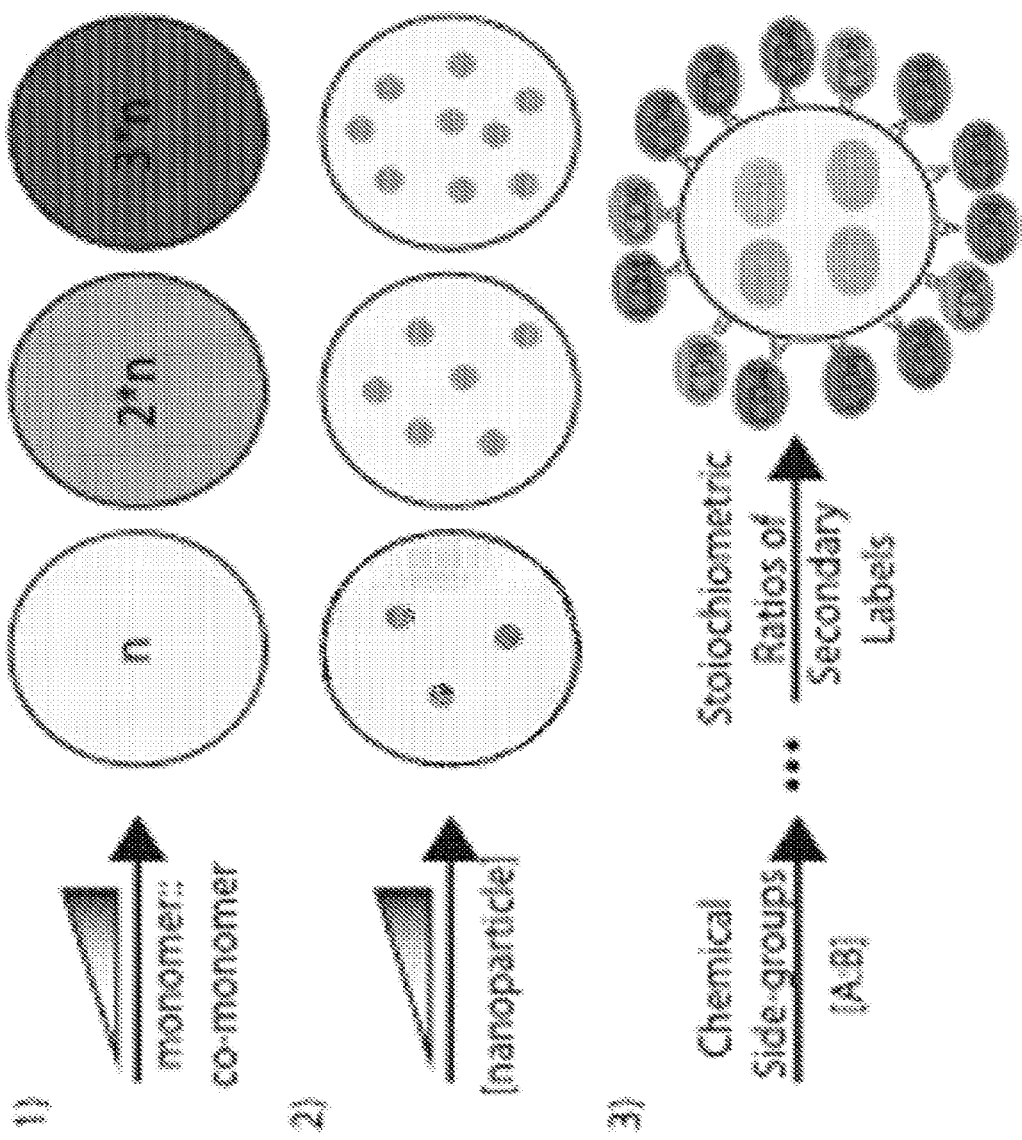
FIG. 4 is a diagram showing variables that can be tuned to encode specific forward and side scatter "barcodes," according to some embodiments.

FIG. 4 is a diagram showing variables that can be tuned to encode specific passive optical (e.g., FSC and/or SSC) "barcodes" on/in groupings of hydrogel particles, according to some embodiments. As shown in the top row (1) of FIG. 4, adjustments in a monomer/co-monomer ratio and cross-linking density can lead to changes in the refractive index of the hydrogel particles (e.g., increasing from n, to 2*n, to 3*n with increasing ratio of monomer::co-monomer). The middle row (2) of FIG. 4 shows that adjustments in nanoparticle composition and concentration can adjust the SSC of the hydrogel particles (e.g., increasing SSC with increased concentration of nanoparticles), and the bottom row (3) of FIG. 4 shows that functionalization of the hydrogel particles with chemical side groups can result in precise, stoichiometric ratios of secondary labels (e.g. fluorophores, proteins, antigens, antibodies) on the hydrogel particles. This feature enables quantitative mean fluorescence intensity (MFI) to be controlled on the particle, a unique feature of the particles described herein.

Figure 5:
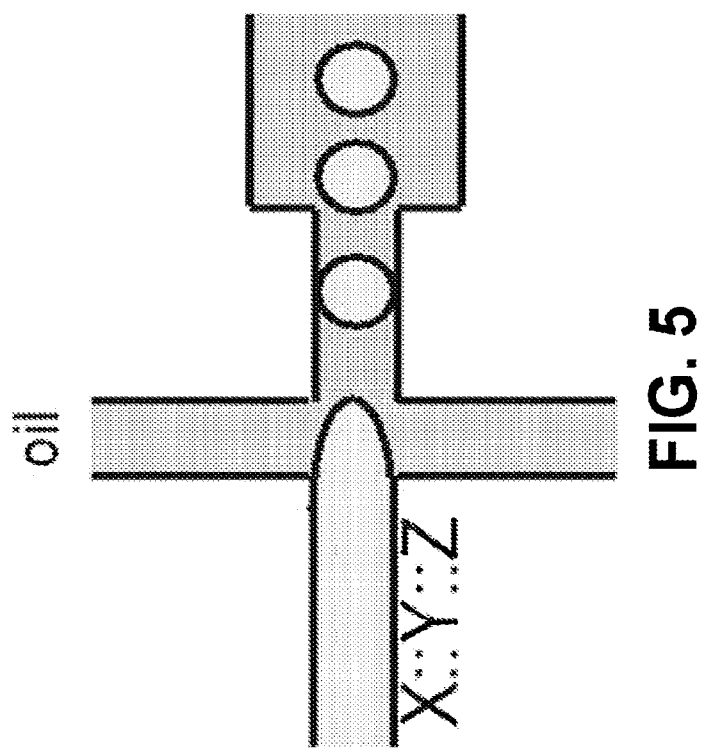
FIG. 5 is a diagram showing particle formation in a microfluidic channel, according to some embodiments.

FIG. 5 is a diagram showing particle formation in an oil-filled microfluidic channel, according to some embodiments.

Hydrogel Particles

In some embodiments, a hydrogel particle includes a hydrogel and is produced by polymerizing a droplet (see the discussion of "drop formation" in relation to FIG. 5). Microfluidic methods of producing a plurality of droplets, including fluidic and rigidified droplets, can include one or more methods described in U.S. Patent Application Publication No. 2011/0218123, titled "Creation of Libraries of Droplets and Related Species," and U.S. Pat. No. 7,294,503, titled "Microfabricated Crossflow Devices and Methods," the contents of each of which are incorporated herein by reference in their entireties, for all purposes. Such methods provide for the generation of a plurality of droplets, each droplet from the plurality of droplets containing a first fluid that is substantially surrounded by a second fluid, where the first fluid and the second fluid are substantially immiscible (e.g., droplets containing an aqueous-based liquid being substantially surrounded by an oil based liquid). In other embodiments, particles can be created via precipitation polymerization, or membrane emulsification.

A plurality of fluidic droplets (e.g., prepared using a microfluidic device) may be polydisperse (e.g., having a range of different sizes), or in some cases, the fluidic droplets may be monodisperse or substantially monodisperse, e.g., having a homogenous distribution of diameters, for instance, such that no more than about 10%, about 5%, about 3%, about 1%, about 0.03%, or about 0.01% of the droplets have an average diameter greater than about 10%, about 5%, about 3%, about 1%, about 0.03%, or about 0.01% of the average diameter. The average diameter of a population of droplets, as used herein, refers to the arithmetic average of the diameters of the droplets.

In some embodiments, a population of hydrogel particles includes a plurality of hydrogel particles, and the population of hydrogel particles is substantially monodisperse.

The term "microfluidic" refers to a device, apparatus or system including at least one fluid channel having a cross-sectional dimension of less than 1 mm, and a ratio of length to largest cross-sectional dimension perpendicular to the channel of at least about 3:1. A microfluidic device comprising a microfluidic channel is especially well suited to preparing a plurality of monodisperse droplets. Cross-flow membrane emulsification and precipitation polymerization are other suitable methods for generating a plurality of monodispersed droplets.

Non-limiting examples of microfluidic systems that may be used with the present invention include those disclosed in U.S. Patent Application Publication No. 2006/0163385 ("Forming and Control of Fluidic Species"), U.S. Patent Application Publication No. 2005/0172476 ("Method and Apparatus for Fluid Dispersion"), U.S. Patent Application Publication No. 2007/000342 ("Electronic Control of Fluidic Species"), International Patent Application Publication No. WO 2006/096571 ("Method and Apparatus for Forming Multiple Emulsions"), U.S. Patent Application Publication No. 2007/0054119 ("Systems and Methods of Forming Particles"), International Patent Application Publication No. WO 2008/121342 ("Emulsions and Techniques for Formation"), and International Patent Application Publication No. WO 2006/078841 ("Systems and Methods for Forming Fluidic Droplets Encapsulated in Particles Such as Colloidal Particles"), the entire contents of each of which are incorporated herein by reference in their entireties, for all purposes.

Droplet size can be related to microfluidic channel size, pore size (in the case of membrane emulsification) and/or flow rate. The microfluidic channel can be any of a variety of sizes, for example, having a largest dimension perpendicular to fluid flow of less than about 5 mm, or less than about 2 mm, or less than about 1 mm, or less than about 500 µm, less than about 200 µm, less than about 100 µm, less than about 60 µm, less than about 50 µm, less than about 40 µm, less than about 30 µm, less than about 25 µm, less than about 10 µm, less than about 3 µm, less than about 1 µm, less than about 300 nm, less than about 100 nm, less than about 30 nm, or less than about 10 nm.

Droplet size can be tuned by adjusting the relative flow rates. In some embodiments, drop diameters are equivalent to the width of the channel, or within about 10%, 15%, 20%, 30%, 40%, 50%, 60%, 70%, 80%, 90%, or 100% the width of the channel.

In some embodiments, the dimensions of a hydrogel particle are substantially similar to the dimensions of a droplet from which it was formed. For example, in some such embodiments, a hydrogel particle has a diameter of less than about 1 µm, less than about 2 µm, less than about 5 µm, less than about 10 µm, less than about 15 µm, less than about 20 µm, less than about 25 µm, less than about 30 µm, less than about 35 µm, less than about 40 µm, less than about 45 µm, less than about 50 µm, less than about 60 µm, less than about 70 µm, less than about 80 µm, less than about 90 µm, less than about 100 µm, less than about 120 µm, less than about 150 µm, less than about 200 µm, less than about 250 µm, less than about 300 µm, less than about 350 µm, less than about 400 µm, less than about 450 µm, less than about 500 µm, less than about 600 µm, less than about 800 µm, or less than 1000 µm in diameter. In some embodiments, a hydrogel particle has a diameter of greater than about 1 µm, greater than about 2 µm, greater than about 5 µm, greater than about 10 µm, greater than about 15 µm, greater than about 20 µm, greater than about 25 µm, greater than about 30 µm, greater than about 35 µm, greater than about 40 µm, greater than about 45 µm, greater than about 50 µm, greater than about 60 µm, greater than about 70 µm, greater than about 80 µm, greater than about 90 µm, greater than about 100 µm, greater than about 120 µm, greater than about 150 µm, greater than about 200 µm, greater than about 250 µm, greater than about 300 µm, greater than about 350 µm, greater than about 400 µm, greater than about 450 µm, greater than about 500 µm, greater than about 600 µm, greater than about 800 µm, or greater than 1000 µm in diameter. In typical embodiments, a hydrogel particle has a diameter in the range of 5 µm to 100 µm.

In some embodiments, one or more hydrogel particles are spherical in shape.

In some embodiments, one or more hydrogel particles have material modulus properties (e.g., elasticity) more closely resembling the corresponding material modulus properties of a target cell (e.g., a human target cell), as compared with the corresponding material modulus properties of a polystyrene bead having the same diameter as the hydrogel particle.

In some embodiments, one or more hydrogel particles do not comprise agarose.

Optical Properties

Passive Optical Properties

The three primary modes of deconvolution for flow cytometry are the two passive optical properties of a particle (forward scattering, FSC, corresponding to the refractive index, or RI; and side scattering, SSC), and the biomarkers present on the surface of a given cell type, which are typically measured via fluorescence. Compositions set forth herein, which allow these properties to be rationally engineered, allow for assay multiplexing, or measuring more than one target (e.g., a cell, a molecule, a biochemical target, etc.) at a time, through deconvolution.

In some embodiments, the refractive index (RI) of one or more hydrogel particles is greater than about 1.10, greater than about 1.15, greater than about 1.20, greater than about 1.25, greater than about 1.30, greater than about 1.35, greater than about 1.40, greater than about 1.45, greater than about 1.50, greater than about 1.55, greater than about 1.60, greater than about 1.65, greater than about 1.70, greater than about 1.75, greater than about 1.80, greater than about 1.85, greater than about 1.90, greater than about 1.95, greater than about 2.00, greater than about 2.10, greater than about 2.20, greater than about 2.30, greater than about 2.40, greater than about 2.50, greater than about 2.60, greater than about 2.70, greater than about 2.80, or greater than about 2.90.

In some embodiments, the RI of one or more hydrogel particles is less than about 1.10, less than about 1.15, less than about 1.20, less than about 1.25, less than about 1.30, less than about 1.35, less than about 1.40, less than about 1.45, less than about 1.50, less than about 1.55, less than about 1.60, less than about 1.65, less than about 1.70, less than about 1.75, less than about 1.80, less than about 1.85, less than about 1.90, less than about 1.95, less than about 2.00, less than about 2.10, less than about 2.20, less than about 2.30, less than about 2.40, less than about 2.50, less than about 2.60, less than about 2.70, less than about 2.80, or less than about 2.90

In some embodiments, the SSC of one or more hydrogel particles can be any value within the full range of possible values as measured by a cytometric device.

In some embodiments, the FSC of one or more hydrogel particles can be any value within the full range of possible values as measured by a cytometric device.

In some embodiments, the FSC of one or more hydrogel particles can be tuned by incorporating a high-refractive index molecule in the hydrogel. Preferred high-refractive index molecules include (but are not limited to) colloidal silica, alkyl acrylate and alkyl methacrylate. Thus, in some embodiments, one or more hydrogel particles include alkyl acrylate and/or alkyl methacrylate. Alkyl acrylates or Alkyl methacrylates can contain 1 to 18, 1 to 8, or 2 to 8, carbon atoms in the alkyl group, such as methyl, ethyl, n-propyl, isopropyl, n-butyl, isobutyl or tert-butyl, 2-ethylhexyl, heptyl or octyl groups. The alkyl group may be branched or linear. High-refractive index molecules can also include vinylarenes such as styrene and methylstyrene, optionally substituted on the aromatic ring with an alkyl group, such as methyl, ethyl or tert-butyl, or with a halogen, such as chlorostyrene.

In some embodiments, the FSC of one or more hydrogel particles is modulated by adjusting the water content present during hydrogel formation. In other embodiments, the FSC of one or more hydrogel particles is modulated by adjusting crosslinking density of the hydrogel. Alternatively or in addition, the FSC of one or more hydrogel particles can be related to particle volume, and thus can be modulated by altering particle diameter, as described herein.

In some embodiments, the SSC of one or more hydrogel particles can be engineered by encapsulating nanoparticles within hydrogels. In some embodiments, a hydrogel particle comprises one or more types of nanoparticles, for example selected from the group consisting of: polymethyl methacrylate (PMMA) nanoparticles, polystyrene (PS) nanoparticles, and silica nanoparticles.

Functionalization of Hydrogel Particles

In some embodiments, in addition to having specific and engineered passive optical properties, hydrogel particles set forth herein can be functionalized, allowing them to mimic the fluorescent properties of labeled cells. In some embodiments, a hydrogel particle comprises a bifunctional monomer, and functionalization of the hydrogel particle occurs via the bifunctional monomer. In some embodiments, a functionalized hydrogel particle comprises a free amine group. In other embodiments, the hydrogel can be functionalized with a protein or peptide which allows for secondary labeling using a reagent, including but not limited to an antibody.

A hydrogel particle can be functionalized with any fluorescent dye, including any of the fluorescent dyes listed in The MolecularProbes® Handbook—A Guide to Fluorescent Probes and Labeling Technologies, the content of which is incorporated herein by reference in its entirety, for all purposes. Functionalization can be mediated by a compound comprising a free amine group, e.g., allylamine, which can be incorporated into a hydrogel particle during the formation process.

Non-limiting examples of suitable fluorescent dyes include: 6-carboxy-4',5'-dichloro-2',7'-dimethoxyfluorescein succinimidyl ester; 5-(and-6)-carboxyeosin; 5-carboxyfluorescein; 6-carboxyfluorescein; 5-(and-6)-carboxyfluorescein; 5-carboxyfluorescein-bis-(5-carboxymethoxy-2-nitrobenzyl)ether, -alanine-carboxamide, or succinimidyl ester; 5-carboxyfluorescein succinimidyl ester; 6-carboxyfluorescein succinimidyl ester; 5-(and-6)-carboxyfluorescein succinimidyl ester; 5-(4,6-dichlorotriazinyl)aminofluorescein; 2',7'-difluorofluorescein; eosin-5-isothiocyanate; erythrosin 5-isothiocyanate; 6-(fluorescein-5-carboxamido)hexanoic acid or succinimidyl ester; 6-(fluorescein-5-(and-6)-carboxamido)hexanoic acid or succinimidyl ester; fluorescein-5-EX succinimidyl ester; fluorescein-5-isothiocyanate; fluorescein-6-isothiocyanate; OregonGreen® 488 carboxylic acid, or succinimidyl ester; Oregon Green® 488 isothiocyanate; Oregon Green® 488-X succinimidyl ester; Oregon Green® 500 carboxylic acid; Oregon Green® 500 carboxylic acid, succinimidyl ester or triethylammonium salt; Oregon Green® 514 carboxylic acid; Oregon Green® 514 carboxylic acid or succinimidyl ester; RhodamineGreen™ carboxylic acid, succinimidyl ester or hydrochloride; Rhodamine Green™ carboxylic acid, trifluoroacetamide or succinimidyl ester; Rhodamine Green™-X succinimidyl ester or hydrochloride; Rhodol- Green™ carboxylic acid, N,0-bis-(trifluoroacetyl) or succinimidyl ester; bis-(4-carboxypiperidinyl) sulfonerhodamine or di(succinimidyl ester); 5-(and-6)carboxynaphtho fluorescein, 5-(and-6)carboxynaphtho fluorescein succinimidyl ester; 5-carboxyrhodamine 6G hydrochloride; 6-carboxyrhodamine 6G hydrochloride, 5-carboxyrhodamine 6G succinimidyl ester; 6-carboxyrhodamine 6G succinimidyl ester; 5-(and-6)-carboxyrhodamine 6G succinimidyl ester; 5-carboxy-2',4',5',7'-tetrabromosulfonefluorescein succinimidyl esteror bis-(diisopropylethylammonium) salt; 5-carboxytetramethylrhodamine; 6-carboxytetramethylrhodamine; 5-(and-6)-carboxytetramethylrhodamine; 5-carboxytetramethylrhodamine succinimidyl ester; 6-carboxytetramethylrhodamine succinimidyl ester; 5-(and-6)-carboxytetramethylrhodamine succinimidyl ester; 6-carboxy-X-rhodamine; 5-carboxy-X-rhodamine succinimidyl ester; 6-carboxy-Xrhodamine succinimidyl ester; 5-(and-6)-carboxy-Xrhodaminesuccinimidyl ester; 5-carboxy-X-rhodamine triethylammonium salt; Lissamine™ rhodamine B sulfonyl chloride; malachite green; isothiocyanate; NANOGOLD® mono(sulfosuccinimidyl ester); QSY® 21 carboxylic acid or succinimidyl ester; QSY® 7 carboxylic acid or succinimidyl ester; Rhodamine Red™-X succinimidyl ester; 6-(tetramethylrhodamine-5-(and-6)-carboxamido)hexanoic acid; succinimidyl ester; tetramethylrhodamine-5-isothiocyanate; tetramethylrhodamine-6-isothiocyanate; tetramethylrhodamine-5-(and-6)-isothiocyanate; Texas Red® sulfonyl; Texas Red® sulfonyl chloride; Texas Red®-X STP ester or sodium salt; Texas Red®-X succinimidyl ester; Texas Red®-X succinimidyl ester; and X-rhodamine-5-(and-6)-isothiocyanate.

Other examples of fluorescent dyes include BODIPY® dyes commercially available from Invitrogen, including, but not limited to BODIPY® FL; BODIPY® TMR STP ester; BODIPY® TR-X STP ester; BODIPY® 630/650-X STPester; BODIPY® 650/665-X STP ester; 6-dibromo-4,4-difluoro-5,7-dimethyl-4-bora-3a,4a-diaza-s-indacene-3-propionic acid succinimidyl ester; 4,4-difluoro-4-bora-3a,4a-diaza-s-indacene-3,5-dipropionic acid; 4,4-difluoro-5,7-dimethyl-4-bora-3a,4a-diaza-s-indacene-3-pentanoic acid; 4,4-difluoro-5,7-dimethyl-4-bora3a,4a-diaza-s-indacene-3-pentanoic acid succinimidyl ester; 4,4-difluoro-5,7-dimethyl-4-bora-3a,4a-diaza-s-indacene-3propionic acid; 4,4-difluoro-5,7-dimethyl-4-bora-3a,4a-diaza-s-indacene-3-propionic acid succinimidyl ester; 4,4difluoro-5,7-dimethyl-4-bora-3a,4a-diaza-s-indacene-3propionic acid; sulfosuccinimidyl ester or sodium salt; 6-((4,4-difluoro-5,7-dimethyl-4-bora-3a,4a-diaza-s-indacene-3propionyl)amino)hexanoic acid; 6-((4,4-difluoro-5,7dimethyl-4-bora-3a,4a-diaza-s-indacene-3-propionyl)amino)hexanoic acid or succinimidyl ester; N-(4,4-difluoro5,7-dimethyl-4-bora-3a,4a-diaza-s-indacene-3-propionyl)cysteic acid, succinimidyl ester or triethylammonium salt; 6-4,4-difluoro-1,3-dimethyl-5-(4-methoxyphenyl)-4-bora3a, 4a4,4-difluoro-5,7-diphenyl-4-bora-3a,4a-diaza-s-indacene-3-propionic acid; 4,4-difluoro-5,7-diphenyl-4-bora3a,4a-diaza-s-indacene-3-propionic acid succinimidyl ester; 4,4-difluoro-5-phenyl-4-bora-3a,4a-diaza-s-indacene-3-propionic acid; succinimidyl ester; 6-((4,4-difluoro-5-phenyl-4bora-3a,4a-diaza-s-indacene-3-propionyl)amino)hexanoic acid or succinimidyl ester; 4,4-difluoro-5-(4-phenyl-1,3butadienyl)-4-bora-3a,4a-diaza-s-indacene-3-propionic acid succinimidyl ester; 4,4-difluoro-5-(2-pyrrolyl)-4-bora-3a,4a-diaza-s-indacene-3-propionic acid succinimidyl ester; 6-(((4,4-difluoro-5-(2-pyrrolyl)-4-bora-3a,4a-diaza-s-indacene-3-yl)styryloxy) acetyl)aminohexanoic acid or succinimidyl ester; 4,4-difluoro-5-styryl-4-bora-3a,4a-diaza-s-indacene-3-propionic acid; 4,4-difluoro-5-styryl-4-bora-3a,4a-diaza-s-indacene-3-propionic acid; succinimidyl ester; 4,4-difluoro-1,3,5,7-tetramethyl-4-bora-3a,4a-diaza-s-indacene-8-propionic acid; 4,4-difluoro-1,3,5,7-tetramethyl-4bora-3a, 4a-diaza-s-indacene-8-propionic acid succinimidyl ester; 4,4-difluoro-5-(2-thienyl)-4-bora-3a,4a-diaza-s-indacene-3-propionic acid succinimidyl ester; 6-(((4-(4,4-difluoro-5-(2-thienyl)-4-bora-3a,4a-diaza-s-indacene-3-yl)phenoxy) acetyl)amino)hexanoic acid or succinimidyl ester; and 6-(((4,4-difluoro-5-(2-thienyl)-4-bora-3a,4a-diaza-s-indacene-3-yl)styryloxy)acetyl)aminohexanoic acid or succinimidyl ester.

Fluorescent dyes can also include, for example, Alexa fluor dyes commercially available from Invitrogen, including but not limited to Alexa Fluor® 350 carboxylic acid; Alexa Fluor® 430 carboxylic acid; Alexa Fluor® 488 carboxylic acid; Alexa Fluor® 532 carboxylic acid; Alexa Fluor® 546 carboxylic acid; Alexa Fluor® 555 carboxylic acid; Alexa Fluor® 568 carboxylic acid; Alexa Fluor® 594 carboxylic acid; Alexa Fluor® 633 carboxylic acid; Alexa Fluor® 647 carboxylic acid; Alexa Fluor® 660 carboxylic acid; and Alexa Fluor® 680 carboxylic acid. Suitable fluorescent dyes can also include, for example, cyanine dyes commercially available from Amersham-Pharmacia Biotech, including, but not limited to Cy3 NHS ester; Cy5 NHS ester; Cy5.5 NHSester; and Cy7 NHS ester.

EXAMPLES

Example I

Generation of Hydrogel Particles

Photomasks for UV lithography were sourced from FineLine Imaging, Inc. and were designed using AutoCad (AutoDesk, Inc.). SU-8 photo resist (Microchem, Inc.) was photo cross-linked on 4" silicon wafers using a collimated UV light source (OAI, Inc.) to create masters for microfluidic device fabrication. PDMS (polydimethylsiloxane, Sigma Aldrich, Inc.) was prepared and formed using soft lithography and microfluidic device fabrication methods (See, e.g., McDonald J C, et al., 2000, Electrophoresis 21:27-40, the contents of which are incorporated herein by reference in their entirety, for all purposes).

Droplets were formed using flow-focusing geometry, in which two oil channels focus a central stream of aqueous monomer solution to break off droplets in a water-in-oil emulsion. A fluorocarbon-oil (Novec 7500 3M, Inc.) was used as the outer, continuous phase liquid for droplet formation. To stabilize droplets before polymerization, a surfactant was added at 0.5% w/w to the oil phase (ammonium carboxylate salt of Krytox 157 FSH, Dupont). To make the basic polyacrylamide gel particle, a central phase of an aqueous monomer solution containing N-acrylamide (1-20% w/v), a cross-linker (N,N'-bisacrylamide, 0.05-1% w/v), an accelerator, and ammonium persulfate (1% w/v) was used. An accelerator, (N,N,N',N'-tetramethylethylenediamine 2% vol %) was added to the oil-phase in order to trigger hydrogel particle polymerization after droplet formation.

Several co-monomers were added to the basic gel formulation to add functionality. Allyl-amine provided primary amine groups for secondary labeling after gel formation. FSC of the droplets was modulated by adjusting the refractive index of the gel by adding co-monomers allyl acrylate and allyl methacrylate. SSC of the droplets was tuned by adding a colloidal suspension of silica nanoparticles and/or PMMA (poly(methyl methacrylate)) particles (~100 nm) to the central aqueous phase prior to polymerization.

Stoichiometric labeling of the hydrogel particles was achieved by utilizing co-monomers containing chemically orthogonal side groups (amine, carboxyl, maleimide, epoxide, alkyne, etc.) for secondary labeling.

Droplets were formed at an average rate of 5 kHz and collected in the fluorocarbon oil phase. After completing polymerization at 50° C. for 30 minutes, the resulting hydrogel particles were washed from the oil into an aqueous solution.

Figure 6:
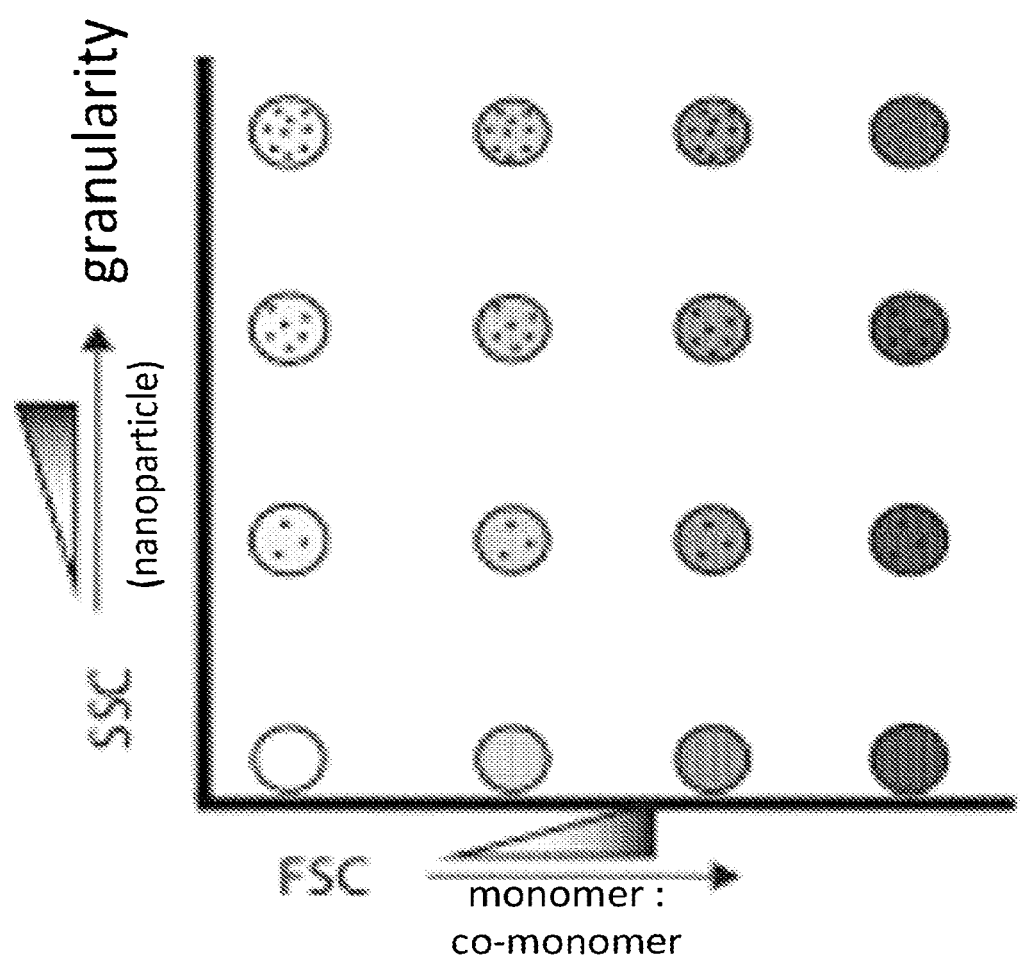
FIG. 6 is a diagram showing an encoding scheme used to create a population of similarly-sized beads that can be de-multiplexed using passive optical properties, according to some embodiments.

FIG. 6 is a diagram showing an encoding scheme used to create a population of similarly-sized beads that can be de-multiplexed using passive optical properties, according to some embodiments. Passive optical barcoding was achieved via FSC and SSC tuning, and by combining particles having unique ratios of FSC/SSC.

Figure 7A:
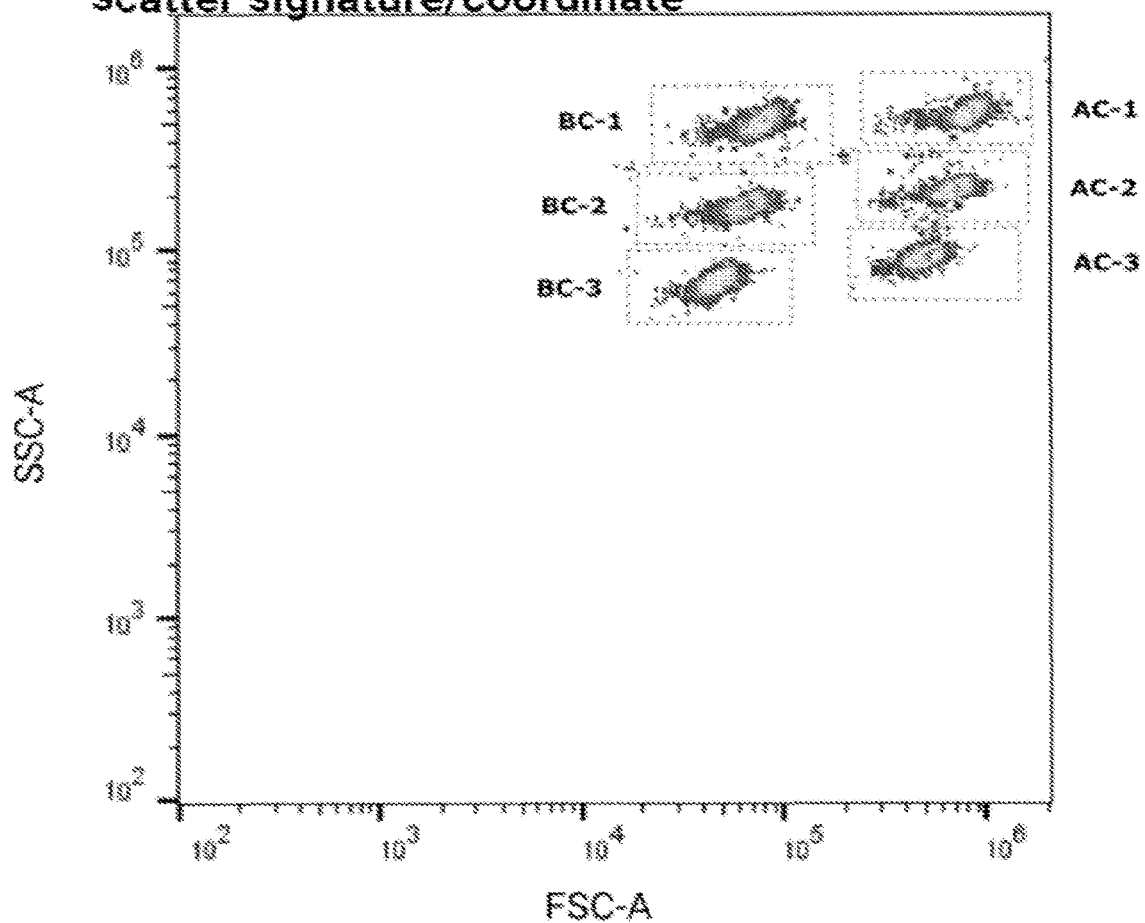
FIG. 7A is a plot showing optical scatter data for multiple populations of identically-sized particles that are distinguishable from one another based on their distinct optical scatter properties.
Figure 7B:
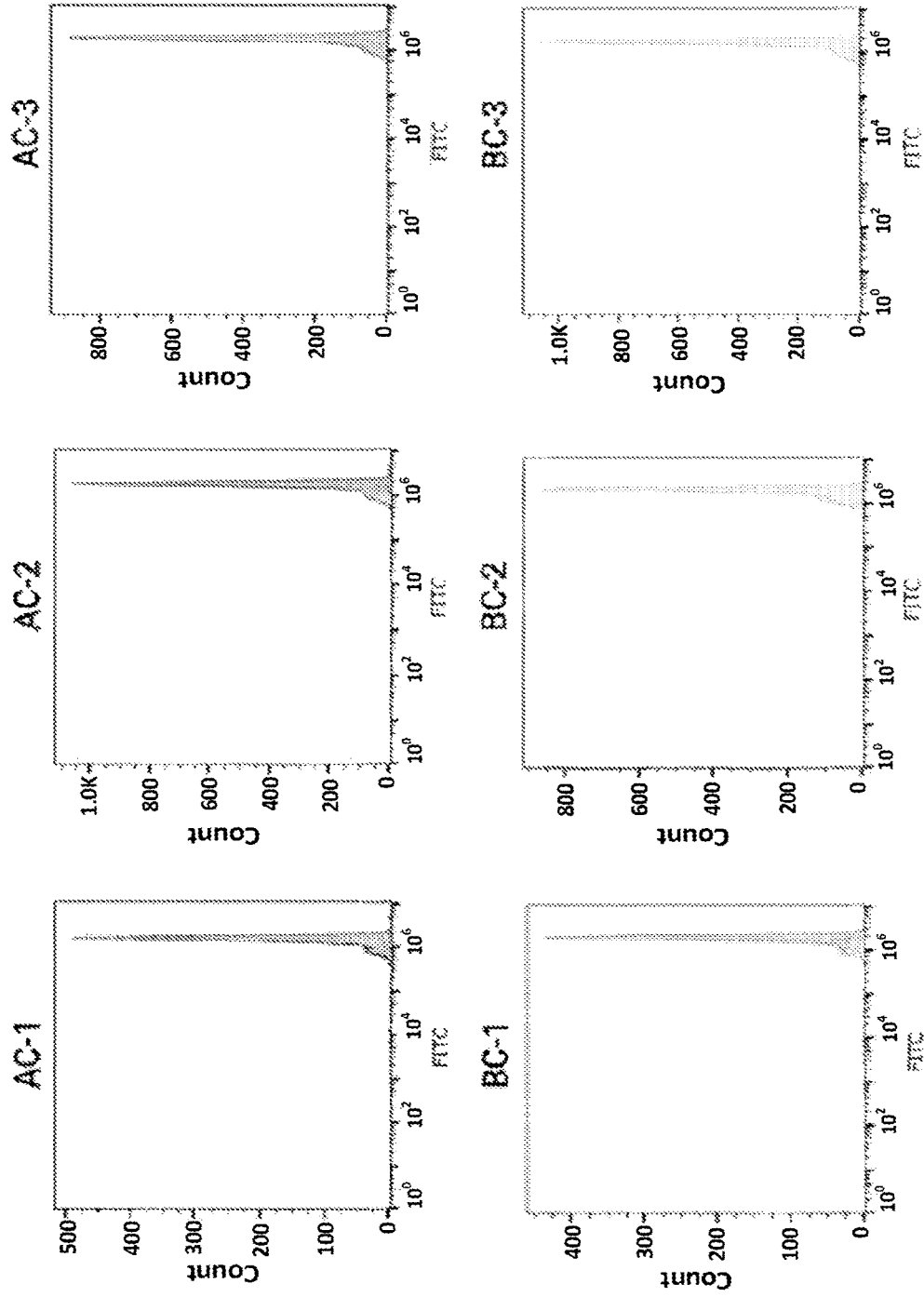
FIG. 7B, by contrast, includes fluorescence plots for each of the multiple particle populations of FIG. 7A, showing that the particle populations of FIG. 7B cannot be distinguished from one another based on fluorescence alone.

FIGS. 7A-7B are characterization plots showing that identically-sized particles can be encoded with distinct passive optical properties. This allows a multiplexed biochemical assay to be deconvoluted using passive optical properties alone. FIG. 7B highlights the inability to distinguish the populations of particles based on fluorescence signal alone, thereby demonstrating biochemical assay multiplexing and demultiplexing using passive optical properties as a primary deconvolution variable, according to some embodiments. FIG. 7A shows multiple synthetic cell populations of the same size, but with distinct passive optical scatter ratios (FSC/SSC). Distinct surface markers were conjugated to each subpopulation and co-incubated with FITC conjugated cognate antibodies. Each biomarker-modified bead population shows an identical fluorescence profile, but can be deconvoluted based on their distinct optical properties to de-multiplex the biochemical assay.

In some embodiments, a composition includes a plurality of hydrogel particles, with each hydrogel particle from the plurality of hydrogel particles having substantially the same diameter. The plurality of hydrogel particles includes a plurality of groups of hydrogel particles, and each group of hydrogel particles from the plurality of groups of hydrogel particles has a different associated one or more values for a passive optical property (e.g., forward scatter and/or side scatter).

The plurality of hydrogel particles may be included in a mixture, and the mixture can be configured to be demultiplexed using only passive optical properties.

In some embodiments, the plurality of hydrogel particles is included in a mixture, and the mixture is configured to be demultiplexed using (1) passive optical properties and (2) fluorescent properties.

In some embodiments, hydrogel particles from at least one group of hydrogel particles from the plurality of groups of hydrogel particles have a refractive index (e.g., an average refractive index or a maximum or minimum refractive index) of greater than about 1.15.

In some embodiments, hydrogel particles from at least one group of hydrogel particles from the plurality of groups of hydrogel particles have a refractive index e.g., an average refractive index or a maximum or minimum refractive index) of greater than about 1.3.

In some embodiments, hydrogel particles from at least one group of hydrogel particles from the plurality of groups of hydrogel particles have a refractive index of greater than about 1.7.

In some embodiments, each hydrogel particle from the plurality of hydrogel particles has a diameter of less than about 1000 μm, or of less than about 100 μm, or of less than about 10 μm.

In some embodiments, the plurality of hydrogel particles includes nanoparticles.

In some embodiments, at least one hydrogel particle from the plurality of hydrogel particles is chemically functionalized.

In some embodiments, at least one hydrogel particle from the plurality of hydrogel particles comprises a free amine group.

In some embodiments, at least one hydrogel particle from the plurality of hydrogel particles comprises allylamine.

In some embodiments, each hydrogel particle from the plurality of hydrogel particles is produce by polymerizing a droplet.

In some embodiments, the plurality of hydrogel particles is a substantially monodisperse population of hydrogel particles.

In some embodiments, a method of performing a multiplexed assay includes assaying a sample using a plurality of optically-encoded hydrogel particles, deconvoluting the plurality of hydrogel particles using a cytometric device and based on passive optical properties of the plurality of hydrogel particles, and determining a plurality of measurements for the sample from a single reaction. Each hydrogel particle from the plurality of hydrogel particles can be functionalized with a different biochemical or chemical target from a set of targets. Alternatively or in addition, each hydrogel particle from the plurality of hydrogel particles can be functionalized with at least one of: an antigen, a protein, a small molecule, or an antibody.

In some embodiments, each group (from a plurality of groups) of hydrogel particles from the plurality of hydrogel particles has a different associated value for a passive optical property (e.g., forward scatter and/or side scatter).

Example 1

Passive Optical Tuning of Hydrogel Particles

As depicted in FIGS. 4 and 6, hydrogel particles are tuned in multiple dimensions to create distinct populations of beads based on their passive optical properties. The beads can be deconvolved using combinations of FSC and SSC. An example matching of three primary subpopulations of white blood cells (lymphocytes, monocytes and granulocytes (neutrophils)) by tuning passive optical properties, independently of particle size, is shown in FIGS. 8A-8B. For the purposes of clarity, all particles in the example of FIGS. 8A-8B are the same diameter. FIG. 8A is a plot of white blood cell (WBC) counts for an actual lysed blood cell population (representing the three subpopulations), and FIG. 8B shows counts for hydrogel particles with tuned passive optical properties and how they mimic the behavior of the lysed whole blood, with no changes made to the instrument settings (e.g., gains, voltages) between data acquisitions. Some end-user applications require an assay bead to look optically similar to a biological cell population. The core technology described herein facilitates the placement of assay beads precisely on the target population of interest, while expanding upon multiplexing capabilities via optical encoding.

Example 2

Tuning of Hydrogel Particle Side Scattering

Figure 9A:
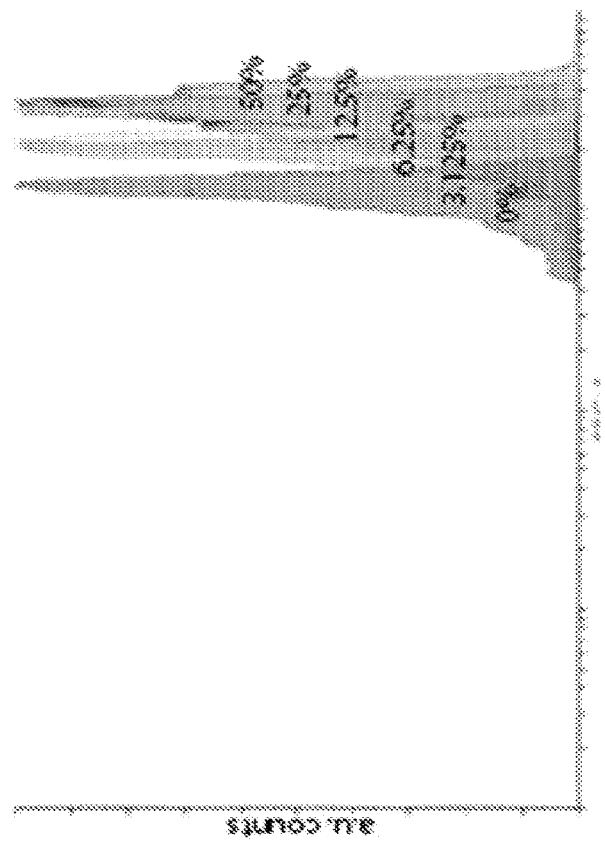
FIG. 9A is a plot of side scatter data for hydrogel particles with tuned passive optical properties.
Figure 9B:
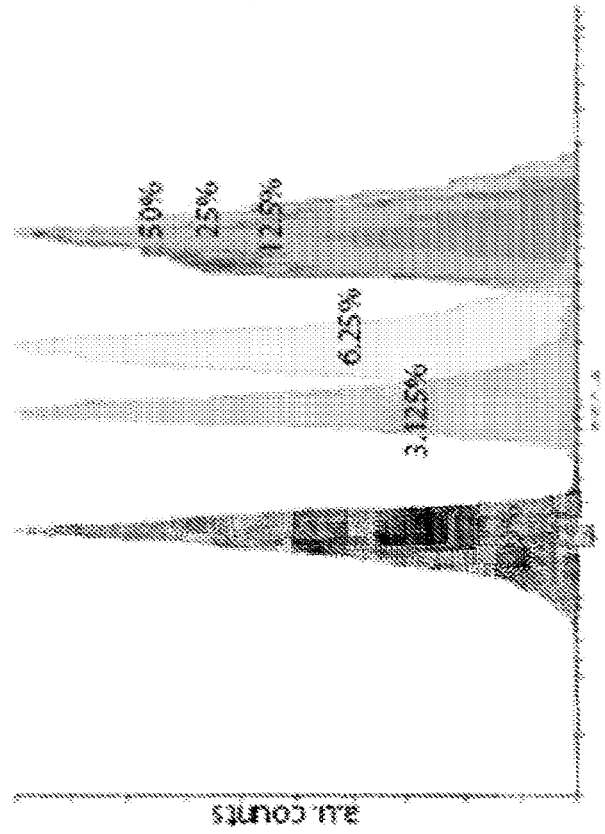
FIG. 9B is a plot of forward scatter data for the hydrogel particles of FIG. 9A.

Colloidal silica was added at 12.5%, 6.25%, 3.125% and 0% to the aqueous fraction of the polymer mix and hydrogel particles were formed as described in Example 1. Forward and side scattering data were obtained using a flow cytometer. The results showed that side scatter signal (FIG. 9A) increased with higher percentages of encapsulated nanoparticles, while forward scatter signal (FIG. 9B) was generally unchanged, demonstrating that side scatter can be tuned independently of forward scatter.

Example 3

Tuning of Hydrogel Particle Forward Scattering

Figures 10A, 10B, 10C:
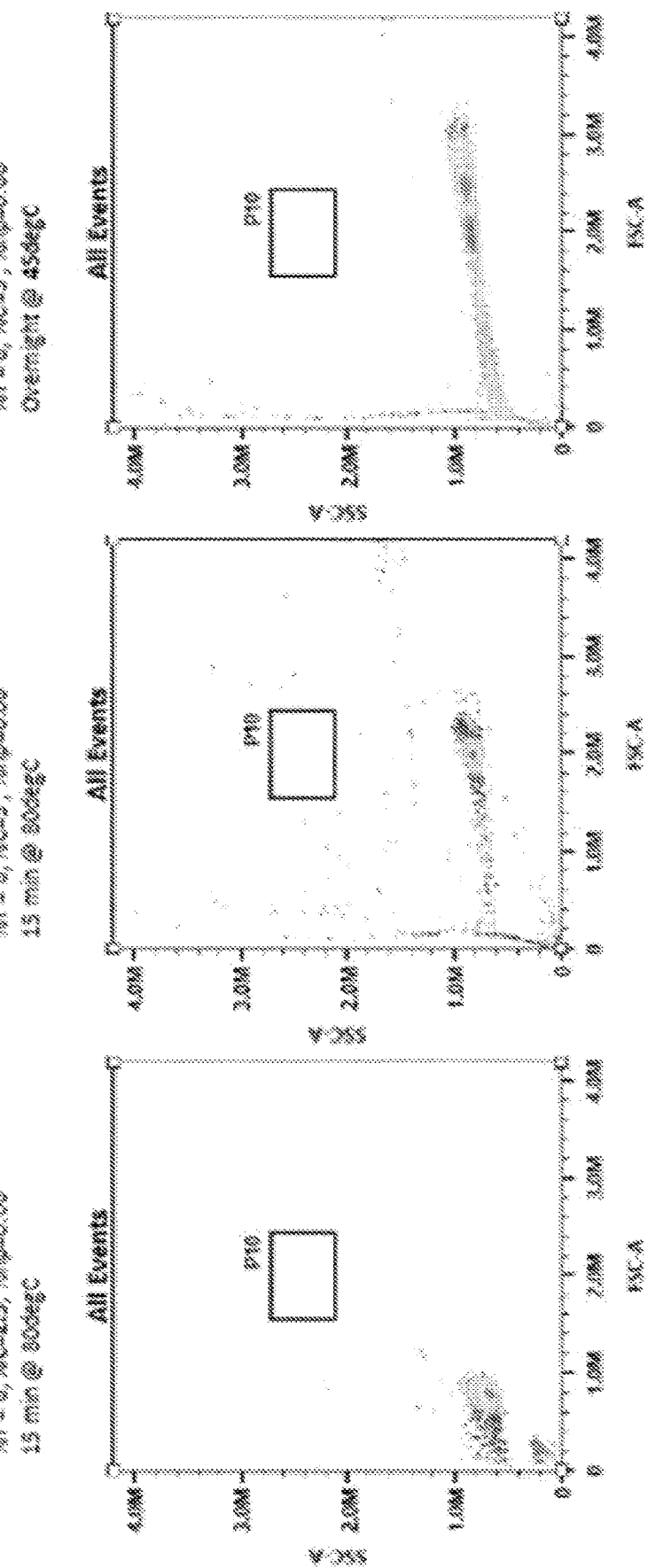
FIG. 10A is a plot of side scatter versus forward scatter for a first acrylamide:bis-acrylamide ratio.
FIG. 10B is a plot of side scatter versus forward scatter for a second acrylamide:bis-acrylamide ratio greater than the first acrylamide:bis-acrylamide ratio.
FIG. 10C is a plot of side scatter versus forward scatter for third acrylamide:bis-acrylamide ratio greater than the second acrylamide:bis-acrylamide ratio.

In this experiment, the percentage of acrylamide:bisacrylamide in the hydrogel composition was varied from between 20 and 40% to tune the refractive index of the hydrogel particles as measured by forward scattering in a flow cytometer. As shown in FIGS. 10A-10C, the forward scattering increased with increasing percentages of acrylamide:bis-acrylamide.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention.

While various embodiments of the system, methods and devices have been described above, it should be understood that they have been presented by way of example only, and not limitation. Where methods and steps described above indicate certain events occurring in a certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made. While the embodiments have been particularly shown and described, it will be understood that various changes in form and details may be made. Although various embodiments have been described as having particular features and/or combinations of components, other embodiments are possible having a combination of any features and/or components from any of embodiments as discussed above.

As used herein, the following terms and expressions are intended to have the following meanings:

The indefinite articles "a" and "an" and the definite article "the" are intended to include both the singular and the plural, unless the context in which they are used clearly indicates otherwise.

"At least one" and "one or more" are used interchangeably to mean that the article may include one or more than one of the listed elements.

Unless otherwise indicated, it is to be understood that all numbers expressing quantities, ratios, and numerical properties of ingredients, reaction conditions, and so forth, are contemplated to be able to be modified in all instances by the term "about".

As used herein, the terms "about" and "approximately" generally mean plus or minus 10% of the value stated, for example about 250 µm would include 225 µm to 275 µm, about 1,000 µm would include 900 µm to 1,100 µm.

In this disclosure, references to items in the singular should be understood to include items in the plural, and vice versa, unless explicitly stated otherwise or clear from the context. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth. The use of any and all examples, or exemplary language ("e.g.," "such as," "including," or the like) provided herein, is intended merely to better illuminate the embodiments and does not pose a limitation on the scope of the embodiments or the claims.

The invention claimed is:

1. A composition for demultiplexing one or more targets based on an encoded optical property, said composition comprising:
    a plurality of populations of hydrogel particles, each population of hydrogel particles having substantially the same average particle diameter,
    wherein each population of hydrogel particles comprises a different forward and/or side scatter optical property, so as to be optically distinguishable from other populations of hydrogel particles within the composition;
    wherein each population of hydrogel particles comprises a different functionalized ligand configured to form a particle target combination with a target selected from the group consisting of a chemical, cellular, or biochemical target;
    wherein each population of the plurality of hydrogel particles is configured to allow for simultaneous demultiplexing of the one or more of the target.

2. The composition of claim 1, wherein the plurality of populations of hydrogel particles are in a mixture, and the mixture is configured to be demultiplexed using only passive optical properties.

3. The composition of claim 1, wherein the plurality of populations of hydrogel particles are in a mixture, and the mixture is configured to be demultiplexed using (1) passive optical properties and (2) fluorescent properties.

4. The composition of claim 1, wherein hydrogel particles from at least one population of hydrogel particles from the plurality of populations of hydrogel particles, have a refractive index of greater than about 1.15.

5. The composition of claim 1, wherein hydrogel particles from at least one population of hydrogel particles from the plurality of populations of hydrogel particles, have a refractive index of greater than about 1.3.

6. The composition of claim 5, wherein each hydrogel particle from the plurality of populations of hydrogel particles, has an average diameter of less than about 100 µm.

7. The composition of claim 1, wherein hydrogel particles from at least one population of hydrogel particles from the plurality of populations of hydrogel particles, have a refractive index of greater than about 1.7.

8. The composition of claim 7, wherein each hydrogel particle from the plurality of populations of hydrogel particles, has an average diameter of less than about 10 µm.

9. The composition of claim 1, wherein each hydrogel particle from the plurality of populations of hydrogel particles has an average diameter of less than about 1000 µm.

10. The composition of claim 1, wherein the plurality of populations of hydrogel particles includes nanoparticles.

11. The composition of claim 1, wherein at least one hydrogel particle from the plurality of populations of hydrogel particles is chemically functionalized.

12. The composition of claim 1, wherein at least one hydrogel particle from the plurality of populations of hydrogel particles comprises a free amine group.

13. The composition of claim 1, wherein at least one hydrogel particle from the plurality of populations of hydrogel particles comprises allylamine.

14. The composition of claim 1, wherein each hydrogel particle from the plurality of populations of hydrogel particles is produced by polymerizing a droplet.

15. The composition of claim 1, wherein the plurality of populations of hydrogel particles are substantially monodisperse.

* * * * *